(12) United States Patent
Kolodner et al.

(10) Patent No.: US 7,374,914 B2
(45) Date of Patent: May 20, 2008

(54) METHOD OF DETECTION OF ALTERATIONS IN MSH5

(75) Inventors: Richard Kolodner, San Diego, CA (US); Nena Winand, Freeville, NY (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 209 days.

(21) Appl. No.: 10/680,386

(22) Filed: Oct. 7, 2003

(65) Prior Publication Data

US 2004/0115715 A1 Jun. 17, 2004

Related U.S. Application Data

(60) Division of application No. 09/470,276, filed on Dec. 22, 1999, now Pat. No. 6,670,460, which is a continuation of application No. PCT/US98/13850, filed on Jul. 2, 1998.

(60) Provisional application No. 60/051,686, filed on Jul. 3, 1997.

(51) Int. Cl.
*C12P 19/34* (2006.01)

(52) U.S. Cl. ............................... 435/91.2

(58) Field of Classification Search ................... None
See application file for complete search history.

(56) References Cited

U.S. PATENT DOCUMENTS 5,710,037 A 1/1998 Vanin et al.

FOREIGN PATENT DOCUMENTS

| WO | WO 95/14085 | | 5/1995 |
| WO | WO 95/15381 | A | 6/1995 |
| WO | WO 95/16793 | A | 6/1995 |
| WO | WO 96/41192 | A | 12/1996 |

OTHER PUBLICATIONS

Wacholder et al (J. Natl. Cancer Institute (2004) 96(6):434-442).*
Lucentini et al (The Scientist (2004) vol. 18).*
Ioannidis (Nature genetics (2001) 29:306-309).*
Yi et al (Biochem. Biophys. Res. Comm. (2005) 332:524-532).*
Hung et al (Proc. Natl. Acad. Sci. (2005) 102(11):4134-4139).*
Bentz et al (Blood (Aug. 1996) 88(4):1437-1444).*
Yeatman et al (Clin. Exp. Metastatis (May 1996) 14:246-252).*
Sargent et al (EMBO Journal (1989) 8(8):2305-2312).*
Therman et al (Human Genetics (1981) 59:93-100).*
N. M. Hollingsworth et al., "MSH5, A Novels MUTS Homolog, Facilitates Meiotic Reciprocal Recombination Between Homologs In *Saccharomyces cerevisiae* But Not Mismatch Repair," *Genes and Development*, 9(14):1728-1739, 1995.
S. Acharya et al., "hMSH2 Forms Specific Mispair-Binding Complexes with hMSH3 and hMSH6," *Proc. Natl. Acad. Sci. USA*, 93:13629-13634, 1996.
B. Liu et al., "Analysis of Mismatch Repair Genes in Hereditary Non-Polyposis Colorectal Cancer Patients," *Nature Medicine*, 2(2)169-174, 1996.
S. Bawa et al., "A Mutation in the MSH5 Gene Results in Alkylation Tolerance," *Cancer Research*, 57:2715-2720, 1997.
Database EMBL Accession No. AF048986, May 6, 1998, C. Her et al., "*Homo sapiens* MutS Homolog 5 (MSH5) mRNA."
Database EMBL Accession No. AF034759, Dec. 2, 1997, T. Bocker et al., "*Homo sapiens* MutS Homolog 5 (MSH5) mRNA."
Database EMBL Accession No. AA120437, Nov. 21, 1996, M Marra et al., "*Mus Musculus* cDNA Clone 541052."
V. Schlensog et al., "The *Escherichia coli* fdv Gene Probably Encoded MutS and is Located at Minute 58.8 Adjacent to the hyp-hyc Gene Cluster," *J. Bacteriol.*, 173(23):7414-7415, 1991.
M. Strand et al., "Destabilization of Tracts of Simple Repetitive DNA in Yeast by Mutations Affecting DNA Mismatch Repair," *Nature*, 365:274-276, 1993.
L.A. Aaltonen et al., "Clues to the Pathogenesis of Familial Colorectal Cancer," *Science*, 260:812-816, 1993.
S.N. Thibodeau et al., "Microsatellite Instability in Cancer of the Proximal Colon," *Science*, 260:816-819, 1993.
P. Peltomäki et al., "Genetic Mapping of a Locus Predisposing to Human Colorectal Cancer," *Science*, 260:810-812, 1993.
M.J. Hughes et al., "The Purification of a Human Mismatch-Binding Protein and Identification of its Associated ATPase and Helicase Activities," *J. Biol. Chem.*, 267(3):23876-23882,1992.
R.A.G. Reenan et al., "Isolation and Characterization of Two *Saccharomyces cerevisiae* Genes Encoding Homologs of the Bacterial HexA and MutS Mismatch Repair proteins," *Genetics*, 132(4):963-973, 1992.
L. New et al., "The Yeast Gene MSH3 Defines a New Class of Eukaryotic MutS Homologues," *Mol. General Genetics*, 239:97-108, 1993.
R. Fishel et al., "The Human Mutator Gene Homolog MSH2 and its Association with Hereditary Nonpolyposis Colon Cancer," *Cell*, 75(5):1027-1038, 1993.
R. Fishel et al., Erratum, *Cell*, 77(1):167, 1994.
F.S. Leach et al., "Mutations of a MutS Homolog in Hereditary Nonpolyposis Colorectal Cancer," *Cell*, 75(6):1215-1225, 1993.
C.E. Bronner et al., "Mutation in the DNA Mismatch Repair Gene Homologue hMLH1 is Associated with Hereditary Non-Polyposis Colon Cancer," *Nature*, 368:258-26, 1994.
J. Jiricny, "Colon Cancer and DNA Repair: Have Mismatches Met Their Match?" *Trends in Genetics*, 10 (5):164-168, 1994.

(Continued)

*Primary Examiner*—Teresa E. Strzelecka
*Assistant Examiner*—Suchira Pande
(74) *Attorney, Agent, or Firm*—Nixon Peabody LLP

(57) ABSTRACT

We have now discovered that mammals have a DNA gene analogous to that existing in bacteria. MSH5 defects or alterations in this mismatch repair pathway in a mammal, such as a human, can be diagnostic of a predisposition to cancer, and prognostic for a particular cancer: We have discovered and sequenced MSH5 in a number of mammals, including humans. This gene can be used in assays, to express gene product, for drug screens, and therapeutically.

17 Claims, No Drawings

OTHER PUBLICATIONS

Hillier et al., (Genbank Accession No. T67203), 1995.

Cross et al., (Genbank Accession No. Z57284 (Oct. 18, 1995).

Sargent et al., "Identification of multiple HTF-island associated genes in the human major histocompatibility complex class III region", EMBO J. 8(8):2305-2312, 1989.

Albertella et al., "Localization of eight additional genes in the human major histocompatability complex, including the gene encoding the casein kinase II b subunit (CSNK2B)", Genomics 36:240-251, 1996.

Lage et al., "Cloning of a human cDNA encoding a protein with high homology to yeast methionyl-tRNA synthetase", Gene (1996) 178:187-189.

* cited by examiner

```
                              SEQUENCE LISTING

<160> NUMBER OF SEQ ID NOS: 104

<210> SEQ ID NO 1
<211> LENGTH: 2900
<212> TYPE: DNA
<213> ORGANISM: Human

<400> SEQUENCE: 1
cgctcctttt gcaggctcgt ggcggtcggt cagcggggcg ttctcccacc tgtagcgact     60
caggttactg aaaaggcggg aaaacgctgc gatggcggca gctggggggag gaggaagata    120 agcgcgtgag gctggggtcc tggcgcgtgg ttggcagagg cagagacata agacgtgcac    180
gactcgcccc acagggcctt cagacccctt ctttccaaag gagcctccaa gctcatggcc    240
tccttaggag cgaacccaag gaggacaccg cagggaccga gacctggggc ggcctcctcc    300
ggtttcccca gcccggcccc agtgccgggc cccaggagg ccgaggagga ggaagtcgag      360
gaggaggagg agctggccga gatccatctg tgtgtgctgt ggaattcagg atacttgggc    420
attgcctact atgatactag tgactccact atccacttca tgccagatgc cccagaccac    480
gagagcctca agcttctcca gagagttctg gatgagatca atccccagtc tgttgttacg    540
agtgccaaac aggatgagaa tatgactcga tttctgggaa agcttgcctc ccaggagcac    600
agagagccta aaagacctga aatcatattt ttgccaagtg tggattttgg tctggagata    660
agcaaacaac gcctcctttc tggaaactac tccttcatcc cagacgccat gactgccact    720
gagaaaatcc tcttcctctc ttccattatt ccctttgact gcctcctcac agttcgagca    780
cttggagggc tgctgaagtt cctgggtcga agaagaatcg gggttgaact ggaagactat    840
aatgtcagcg tccccatcct gggctttaag aaatttatgt tgactcatct ggtgaacata    900
gatcaagaca cttacagtgt tctacagatt tttaagagtg agtctcaccc ctcagtgtac    960
aaagtggcca gtgactgaa ggagggctc agcctctttg gaatcctcaa cagatgccac    1020
tgtaagtggg gagagaagct gctcaggcta tggttcacac gtccgactca tgacctgggg   1080
gagctcagtt ctcgtctgga cgtcattcag ttttttctgc tgccccagaa tctggacatg   1140
gctcagatgc tgcatcggct cctgggtcac atcaagaacg tgcctttgat tctgaaacgc   1200
atgaagttgt cccacaccaa ggtcagcgac tggcaggttc tctacaagac tgtgtacagt   1260
gccctgggcc tgagggatgc ctgccgctcc ctgccgcagt ccatccagct ctttcgggac   1320
attgcccaag agttctctga tgacctgcac catatcgcca gctcattgg gaaagtagtg    1380 gactttgagg gcagccttgc tgaaaatcgc ttcacagtcc tccccaacat agatcctgaa   1440
attgatgaga aaaagcgaag actgatggga cttcccagtt tccttactga ggttgcccgc   1500
aaggagctgg agaatctgga ctcccgtatt ccttcatgca gtgtcatcta catccctctg   1560
attggcttcc ttctttctat tccccgcctg ccttccatgg tagaggccag tgactttgag   1620
attaatggac tggacttcat gtttctctca gaggagaagc tgcactatcg tagtgcccga   1680
accaaggagc tggatgcatt gctgggggac ctgcactgcg agatccggga ccaggagacg   1740
ctgctgatgt accagctaca gtgccaggtg ctggcacgag cagctgtctt aacccgagta   1800
ttggaccttg cctcccgcct ggacgtcctg ctggctcttg ccagtgctgc ccgggactat   1860
```

-continued

```
ggctactcaa ggccgcgtta ctccccacaa gtccttgggg tacgaatcca gaatggcaga      1920
catcctctga tggaactctg tgccgaacc tttgtgccca actccacaga atgtggtggg       1980
gacaaaggga gggtcaaagt catcactgga cccaactcat cagggaagag catataccTC     2040
aaacaggtag gcttgatcac attcatggcc ctggtaggca gctttgtgcc agcagaggag    2100
gccgaaattg gggcagtaga cgccatcttc acacgaattc atagctgcga atccatctcc   2160
cttggcctct ccaccttcat gatcgacctc aaccaggtgg cgaaagcagt gaacaatgcc    2220
actgcacagt cgctggtcct tattgatgaa tttggaaagg gaaccaacac ggtggatggg    2280
ctcgcgcttc tggccgctgt gctccgacac tggctggcac gtggacccac atgcccccac    2340
atctttgtgg ccaccaactt tctgagcctt gttcagctac aactgctgcc acaagggccc    2400
ctggtgcagt atttgaccat ggagacctgt gaggatggca acgatcttgt cttcttctat    2460
caggtttgcg aaggtgttgc gaaggccagc catgcctccc acacagctgc ccaggctggg    2520
cttcctgaca gcttgtggc tcgtggcaag gaggtctcag atttgatccg cagtggaaaa      2580
cccatcaagc ctgtcaagga tttgctaaag aagaaccaaa tggaaaattg ccagacatta    2640
gtggataagt ttatgaaact ggatttggaa gatcctaacc tggacttgaa cgttttcatg    2700
agccaggaag tgctgcctgc tgccaccagc atcctgtgag agtccttcca gtgtcctccc    2760
cagcctcctg agactccggt gggctgccat gccctctttg tttccttatc tccctcagac    2820
gcagagtttt tagtttctct agaaattttg tttcatatta ggaataaagt ttatttttgaa    2880 gaaaaaaaaa aaaaaaaaaa                                                 2900
```

<210> SEQ ID NO 2
<211> LENGTH: 834
<212> TYPE: PRT
<213> ORGANISM: Human

<400> SEQUENCE: 2

```
Met Ala Ser Leu Gly Ala Asn Pro Arg Arg Thr Pro Gln Gly Pro Arg
  1               5                  10                  15

Pro Gly Ala Ala Ser Ser Gly Phe Pro Ser Pro Ala Pro Val Pro Gly
                 20                  25                  30

Pro Arg Glu Ala Glu Glu Glu Val Glu Glu Glu Glu Leu Ala
             35                  40                  45

Glu Ile His Leu Cys Val Leu Trp Asn Ser Gly Tyr Leu Gly Ile Ala
     50                  55                  60

Tyr Tyr Asp Thr Ser Asp Ser Thr Ile His Phe Met Pro Asp Ala Pro
 65                  70                  75                  80

Asp His Glu Ser Leu Lys Leu Leu Gln Arg Val Leu Asp Glu Ile Asn
                 85                  90                  95

Pro Gln Ser Val Val Thr Ser Ala Lys Gln Asp Glu Asn Met Thr Arg
            100                 105                 110

Phe Leu Gly Lys Leu Ala Ser Gln Glu His Arg Glu Pro Lys Arg Pro
        115                 120                 125

Glu Ile Ile Phe Leu Pro Ser Val Asp Phe Gly Leu Glu Ile Ser Lys
    130                 135                 140

Gln Arg Leu Leu Ser Gly Asn Tyr Ser Phe Ile Pro Asp Ala Met Thr
145                 150                 155                 160

Ala Thr Glu Lys Ile Leu Phe Leu Ser Ser Ile Ile Pro Phe Asp Cys
                165                 170                 175

Leu Leu Thr Val Arg Ala Leu Gly Gly Leu Leu Lys Phe Leu Gly Arg
```

-continued

```
                    180                 185                 190
Arg Arg Ile Gly Val Glu Leu Glu Asp Tyr Asn Val Ser Val Pro Ile
            195                 200                 205

Leu Gly Phe Lys Lys Phe Met Leu Thr His Leu Val Asn Ile Asp Gln
        210                 215                 220

Asp Thr Tyr Ser Val Leu Gln Ile Phe Lys Ser Glu Ser His Pro Ser
225                 230                 235                 240

Val Tyr Lys Val Ala Ser Gly Leu Lys Glu Gly Leu Ser Leu Phe Gly
                245                 250                 255

Ile Leu Asn Arg Cys His Cys Lys Trp Gly Glu Lys Leu Leu Arg Leu
            260                 265                 270

Trp Phe Thr Arg Pro Thr His Asp Leu Gly Glu Leu Ser Ser Arg Leu
        275                 280                 285

Asp Val Ile Gln Phe Phe Leu Leu Pro Gln Asn Leu Asp Met Ala Gln
    290                 295                 300

Met Leu His Arg Leu Leu Gly His Ile Lys Asn Val Pro Leu Ile Leu
305                 310                 315                 320

Lys Arg Met Lys Leu Ser His Thr Lys Val Ser Asp Trp Gln Val Leu
                325                 330                 335

Tyr Lys Thr Val Tyr Ser Ala Leu Gly Leu Arg Asp Ala Cys Arg Ser
            340                 345                 350

Leu Pro Gln Ser Ile Gln Leu Phe Arg Asp Ile Ala Gln Glu Phe Ser
        355                 360                 365

Asp Asp Leu His His Ile Ala Ser Leu Ile Gly Lys Val Val Asp Phe
    370                 375                 380

Glu Gly Ser Leu Ala Glu Asn Arg Phe Thr Val Leu Pro Asn Ile Asp
385                 390                 395                 400

Pro Glu Ile Asp Glu Lys Lys Arg Arg Leu Met Gly Leu Pro Ser Phe
                405                 410                 415

Leu Thr Glu Val Ala Arg Lys Glu Leu Glu Asn Leu Asp Ser Arg Ile
            420                 425                 430

Pro Ser Cys Ser Val Ile Tyr Ile Pro Leu Ile Gly Phe Leu Leu Ser
        435                 440                 445

Ile Pro Arg Leu Pro Ser Met Val Glu Ala Ser Asp Phe Glu Ile Asn
    450                 455                 460

Gly Leu Asp Phe Met Phe Leu Ser Glu Glu Lys Leu His Tyr Arg Ser
465                 470                 475                 480

Ala Arg Thr Lys Glu Leu Asp Ala Leu Leu Gly Asp Leu His Cys Glu
                485                 490                 495

Ile Arg Asp Gln Glu Thr Leu Leu Met Tyr Gln Leu Gln Cys Gln Val
            500                 505                 510

Leu Ala Arg Ala Ala Val Leu Thr Arg Val Leu Asp Leu Ala Ser Arg
        515                 520                 525

Leu Asp Val Leu Leu Ala Leu Ala Ser Ala Ala Arg Asp Tyr Gly Tyr
    530                 535                 540

Ser Arg Pro Arg Tyr Ser Pro Gln Val Leu Gly Val Arg Ile Gln Asn
545                 550                 555                 560

Gly Arg His Pro Leu Met Glu Leu Cys Ala Arg Thr Phe Val Pro Asn
                565                 570                 575

Ser Thr Glu Cys Gly Gly Asp Lys Gly Arg Val Lys Val Ile Thr Gly
            580                 585                 590

Pro Asn Ser Ser Gly Lys Ser Ile Tyr Leu Lys Gln Val Gly Leu Ile
        595                 600                 605
```

```
Thr Phe Met Ala Leu Val Gly Ser Phe Val Pro Ala Glu Glu Ala Glu
    610                 615                 620
Ile Gly Ala Val Asp Ala Ile Phe Thr Arg Ile His Ser Cys Glu Ser
625                 630                 635                 640
Ile Ser Leu Gly Leu Ser Thr Phe Met Ile Asp Leu Asn Gln Val Ala
                645                 650                 655
Lys Ala Val Asn Asn Ala Thr Ala Gln Ser Leu Val Leu Ile Asp Glu
            660                 665                 670
Phe Gly Lys Gly Thr Asn Thr Val Asp Gly Leu Ala Leu Leu Ala Ala
        675                 680                 685
Val Leu Arg His Trp Leu Ala Arg Gly Pro Thr Cys Pro His Ile Phe
    690                 695                 700
Val Ala Thr Asn Phe Leu Ser Leu Val Gln Leu Gln Leu Leu Pro Gln
705                 710                 715                 720
Gly Pro Leu Val Gln Tyr Leu Thr Met Glu Thr Cys Glu Asp Gly Asn
                725                 730                 735
Asp Leu Val Phe Phe Tyr Gln Val Cys Glu Gly Val Ala Lys Ala Ser
            740                 745                 750
His Ala Ser His Thr Ala Ala Gln Ala Gly Leu Pro Asp Lys Leu Val
        755                 760                 765
Ala Arg Gly Lys Glu Val Ser Asp Leu Ile Arg Ser Gly Lys Pro Ile
    770                 775                 780
Lys Pro Val Lys Asp Leu Leu Lys Lys Asn Gln Met Glu Asn Cys Gln
785                 790                 795                 800
Thr Leu Val Asp Lys Phe Met Lys Leu Asp Leu Glu Asp Pro Asn Leu
                805                 810                 815
Asp Leu Asn Val Phe Met Ser Gln Glu Val Leu Pro Ala Ala Thr Ser
            820                 825                 830
Ile Leu

<210> SEQ ID NO 3
<211> LENGTH: 29
<212> TYPE: DNA
<213> ORGANISM: Human

<400> SEQUENCE: 3
ttccaaaggg taacctccgc gtgacagaa                                    29

<210> SEQ ID NO 4
<211> LENGTH: 29
<212> TYPE: DNA
<213> ORGANISM: Human

<400> SEQUENCE: 4
ctggccgagg tctctgaggg gagtagaaa                                    29

<210> SEQ ID NO 5
<211> LENGTH: 29
<212> TYPE: DNA
<213> ORGANISM: Human

<400> SEQUENCE: 5
tccagagagg tggggatgga accatgaat                                    29

<210> SEQ ID NO 6
<211> LENGTH: 29
<212> TYPE: DNA
```

<213> ORGANISM: Human

<400> SEQUENCE: 6
gaaagcttgg taaggacttg gtaaaggat                                    29

<210> SEQ ID NO 7
<211> LENGTH: 29
<212> TYPE: DNA
<213> ORGANISM: Human

<400> SEQUENCE: 7
tggattttgg tatctccttc cttttgctt                                    29

<210> SEQ ID NO 8
<211> LENGTH: 29
<212> TYPE: DNA
<213> ORGANISM: Human

<400> SEQUENCE: 8
ctcctcacag tgagattggt cctggggga                                    29

<210> SEQ ID NO 9
<211> LENGTH: 29
<212> TYPE: DNA
<213> ORGANISM: Human

<400> SEQUENCE: 9
atttatgttg taggtgattc accccaacc                                    29

<210> SEQ ID NO 10
<211> LENGTH: 29
<212> TYPE: DNA
<213> ORGANISM: Human

<400> SEQUENCE: 10
cacttacagg taaagaggtg gaggcatgc                                    29

<210> SEQ ID NO 11
<211> LENGTH: 29
<212> TYPE: DNA
<213> ORGANISM: Human

<400> SEQUENCE: 11
gcctctttgg taggtgtgcc ccatccctc                                    29

<210> SEQ ID NO 12
<211> LENGTH: 29
<212> TYPE: DNA
<213> ORGANISM: Human

<400> SEQUENCE: 12
gctgctcagg tgagtgggtc ccacacata                                    29

<210> SEQ ID NO 13
<211> LENGTH: 29
<212> TYPE: DNA
<213> ORGANISM: Human

<400> SEQUENCE: 13
aacgtgcctg tgagcccagg gtggagggc                                    29

<210> SEQ ID NO 14
<211> LENGTH: 29

```
<212> TYPE: DNA
<213> ORGANISM: Human

<400> SEQUENCE: 14
ctctacaagg taaggccttc cttcttgaa                                    29

<210> SEQ ID NO 15
<211> LENGTH: 29
<212> TYPE: DNA
<213> ORGANISM: Human

<400> SEQUENCE: 15
gggaaagtag tgagtagaag gaaaaaggg                                    29

<210> SEQ ID NO 16
<211> LENGTH: 29
<212> TYPE: DNA
<213> ORGANISM: Human

<400> SEQUENCE: 16
ttgatgagag tgagtgttgg gtgtggatg                                    29

<210> SEQ ID NO 17
<211> LENGTH: 29
<212> TYPE: DNA
<213> ORGANISM: Human

<400> SEQUENCE: 17
atccctctgg tgagggcagg agagtgggt                                    29

<210> SEQ ID NO 18
<211> LENGTH: 29
<212> TYPE: DNA
<213> ORGANISM: Human

<400> SEQUENCE: 18
gacttcatgg taagaccctc aacctctgt                                    29

<210> SEQ ID NO 19
<211> LENGTH: 29
<212> TYPE: DNA
<213> ORGANISM: Human

<400> SEQUENCE: 19
agatccgggg tgaggaaaag ccagaggtt                                    29

<210> SEQ ID NO 20
<211> LENGTH: 29
<212> TYPE: DNA
<213> ORGANISM: Human

<400> SEQUENCE: 20
gaatggcagg taagaataga ggcgggtgg                                    29

<210> SEQ ID NO 21
<211> LENGTH: 29
<212> TYPE: DNA
<213> ORGANISM: Human

<400> SEQUENCE: 21
ctcaaacagg tgaggagaag ccctgcagc                                    29

<210> SEQ ID NO 22
```

```
<211> LENGTH: 29
<212> TYPE: DNA
<213> ORGANISM: Human

<400> SEQUENCE: 22
ctcaaccagg tcaaagggaa caaagggag                                29

<210> SEQ ID NO 23
<211> LENGTH: 29
<212> TYPE: DNA
<213> ORGANISM: Human

<400> SEQUENCE: 23
accaacacgg tgaggggaga aactgatga                                29

<210> SEQ ID NO 24
<211> LENGTH: 29
<212> TYPE: DNA
<213> ORGANISM: Human

<400> SEQUENCE: 24
cagtatttgg tgaggagacc aatctagct                                29

<210> SEQ ID NO 25
<211> LENGTH: 29
<212> TYPE: DNA
<213> ORGANISM: Human

<400> SEQUENCE: 25
ggcaaggagg tgatgagatc caaatgtgc                                29

<210> SEQ ID NO 26
<211> LENGTH: 29
<212> TYPE: DNA
<213> ORGANISM: Human

<400> SEQUENCE: 26
aatggaaaag tgcgtatatg gccccagtg                                29

<210> SEQ ID NO 27
<211> LENGTH: 29
<212> TYPE: DNA
<213> ORGANISM: Human

<400> SEQUENCE: 27 ctcactttt gcatccgcag agcctccaa                                29

<210> SEQ ID NO 28
<211> LENGTH: 29
<212> TYPE: DNA
<213> ORGANISM: Human

<400> SEQUENCE: 28
ctttcttcct tgctggacag atccatctg                                29

<210> SEQ ID NO 29
<211> LENGTH: 29
<212> TYPE: DNA
<213> ORGANISM: Human

<400> SEQUENCE: 29
gatctctgtt ctccttccag ttctggatg                                29
```

<210> SEQ ID NO 30
<211> LENGTH: 29
<212> TYPE: DNA
<213> ORGANISM: Human

<400> SEQUENCE: 30
ttttctttcc tcccccacag cctcccagg                               29

<210> SEQ ID NO 31
<211> LENGTH: 29
<212> TYPE: DNA
<213> ORGANISM: Human

<400> SEQUENCE: 31
tgcttgcctc cctcaaatag gtctggaga                               29

<210> SEQ ID NO 32
<211> LENGTH: 29
<212> TYPE: DNA
<213> ORGANISM: Human

<400> SEQUENCE: 32
cactgctgat cccctcccag gttcgagca                               29

<210> SEQ ID NO 33
<211> LENGTH: 29
<212> TYPE: DNA
<213> ORGANISM: Human

<400> SEQUENCE: 33
tttttgtttt ctgtcctcag gactcatct                               29

<210> SEQ ID NO 34
<211> LENGTH: 29
<212> TYPE: DNA
<213> ORGANISM: Human

<400> SEQUENCE: 34
cctccatttc tcctcgacag tgttctaca                               29

<210> SEQ ID NO 35
<211> LENGTH: 29
<212> TYPE: DNA
<213> ORGANISM: Human

<400> SEQUENCE: 35
cctgccttat ccctcacaag aatcctcaa                               29

<210> SEQ ID NO 36
<211> LENGTH: 29
<212> TYPE: DNA
<213> ORGANISM: Human

<400> SEQUENCE: 36
acccaaaccc tcacttccag gctatggtt                               29

<210> SEQ ID NO 37
<211> LENGTH: 29
<212> TYPE: DNA
<213> ORGANISM: Human

<400> SEQUENCE: 37
gtaaccttgt ctgactgtag ttgattctg                               29

```
<210> SEQ ID NO 38
<211> LENGTH: 29
<212> TYPE: DNA
<213> ORGANISM: Human

<400> SEQUENCE: 38
tttttgtgtt tctctcacag actgtgtac                              29

<210> SEQ ID NO 39
<211> LENGTH: 29
<212> TYPE: DNA
<213> ORGANISM: Human

<400> SEQUENCE: 39
aacagtactt atctcctcag gtggactttt                             29

<210> SEQ ID NO 40
<211> LENGTH: 29
<212> TYPE: DNA
<213> ORGANISM: Human

<400> SEQUENCE: 40
cctgtcttcc accctcgtag aaaagcgaa                              29

<210> SEQ ID NO 41
<211> LENGTH: 29
<212> TYPE: DNA
<213> ORGANISM: Human

<400> SEQUENCE: 41
ctcctcttta ctctccccag attggcttc                              29

<210> SEQ ID NO 42
<211> LENGTH: 29
<212> TYPE: DNA
<213> ORGANISM: Human

<400> SEQUENCE: 42
ctttgaaccc ctgtacccag tttctctca                              29

<210> SEQ ID NO 43
<211> LENGTH: 29
<212> TYPE: DNA
<213> ORGANISM: Human

<400> SEQUENCE: 43
ccttcctcac ccactcccag accaggaga                              29

<210> SEQ ID NO 44
<211> LENGTH: 29
<212> TYPE: DNA
<213> ORGANISM: Human

<400> SEQUENCE: 44
tgcctctccg cccactgcag acatcctct                              29

<210> SEQ ID NO 45
<211> LENGTH: 29
<212> TYPE: DNA
<213> ORGANISM: Human

<400> SEQUENCE: 45
ctgtctcctt ccctattcag gtaggcttg                              29
```

<210> SEQ ID NO 46
<211> LENGTH: 29
<212> TYPE: DNA
<213> ORGANISM: Human

<400> SEQUENCE: 46 gtccaccttea tacccagcag gtggcgaaa                                    29

<210> SEQ ID NO 47
<211> LENGTH: 29
<212> TYPE: DNA
<213> ORGANISM: Human

<400> SEQUENCE: 47
aacctctgcc ctctttgcag gtggatggg                                     29

<210> SEQ ID NO 48
<211> LENGTH: 29
<212> TYPE: DNA
<213> ORGANISM: Human

<400> SEQUENCE: 48
gtcttttatt ctcttttaag accatggag                                     29

<210> SEQ ID NO 49
<211> LENGTH: 29
<212> TYPE: DNA
<213> ORGANISM: Human

<400> SEQUENCE: 49
caccttcttg cttgtcctag gtctcagat                                     29

<210> SEQ ID NO 50
<211> LENGTH: 29
<212> TYPE: DNA
<213> ORGANISM: Human

<400> SEQUENCE: 50
cgattttctc tcttcttcag ttgccagac                                     29

<210> SEQ ID NO 51
<211> LENGTH: 20
<212> TYPE: DNA
<213> ORGANISM: Human

<400> SEQUENCE: 51
gaatggcaga catcctctga                                               20

<210> SEQ ID NO 52
<211> LENGTH: 22
<212> TYPE: DNA
<213> ORGANISM: Human

<400> SEQUENCE: 52
ggtatatgct cttccctgat ga                                            22

<210> SEQ ID NO 53
<211> LENGTH: 2576
<212> TYPE: DNA
<213> ORGANISM: Human

<400> SEQUENCE: 53

```
ggcttggggc ggttggtcag ggaggtggat cgtcgcggct gagagtcgcc gagcccatgg    60
ctttcagagc gaccccaggc cggacgccgc cgggacccgg acccagatcc ggaatcccct   120
cagccagctt ccccagccct cagccccaa tggcggggcc tggaggtatc gaggaagagg   180
acgaggagga gcccgccgag atccatctgt gcgtgctgtg gagctcggga tacctgggca   240
ttgcttacta tgacactagt gactccacta tccacttcat gccagatgcc ccagaccacg   300
agagcctaaa gcttctccag agagttctgg atgaaatcaa cccccagtct gttgtcacaa   360
gtgccaaaca ggatgaggct atgactcgat ttctagggaa gcttgcctct gaggagcaca   420
gagagccaaa gggacctgaa atcatacttc tgccaagcgt ggattttggt ccagagataa   480
gcaaacagcg tctcctttcc ggaaactact ccttcatctc agactccatg actgctactg   540
agaaaatcct tttcctctcc tccattattc cctttgactg tgtcctcacg gtccgggcac   600
ttggaggact gctcaagttc ctgagtcgaa gaagaattgg ggttgaactg gaagactatg   660
atgttggcgt ccctatcctg ggattcaaga gtttgtatt gacccatctg gtgagcatag   720
atcaagacac ttacagcgtt ctacagattt tcaagagtga gtctcacccc tcggtgtaca   780
aagtagccaa tgggctgaag gaggggctca gccttttttgg aatcctcaac agatgccgct   840
gtaagtgggg acagaagctg ctcaggctgt ggtttacacg tccaacccgg gagctaaggg   900
aactcaattc ccgactggat gtcattcagt tcttcctgat gcctcagaac ctggacatgg   960
cccagatgct gcaccgactc ctgagccaca tcaagaatgt gcctctgatt ctgaaacgca  1020
tgaagttgtc ccacaccaag gtcagtgact ggcaggtcct ctacaagact gtgtacagtg  1080
ctctcggcct gagggatgcc tgccgttctc tgccacagtc catccagctt tttcaggaca  1140
ttgcccagga gttctctgac gacctgcatc acattgccag cctcatcggg aaggtggtgg  1200
actttgagga aagtcttgct gaaaatcgct tcacagtcct ccctaacata gaccctgaca  1260
tagatgccaa gaagcgaagg ctgatagggc ttccgagctt cctcactgaa gttgctcaga  1320
aggagctgga gaacctggac tctcgcatcc cctcatgcag tgtcatctac atccctctga  1380
ttggcttcct tctttccatt ccccgcttgc ctttcatggt ggaagctagt gactttgaga  1440
ttgaggggct ggacttcatg tttctctcag aggacaagct gcactatcgt agcgcccgga  1500
ccaaggagct ggacacgctg ctgggagacc tgcactgtga gatccgggac caggagactc  1560
tgttgatgta ccagctgcag tgccaggtgc tggcacgggc ttcggtcttg actcgggtat  1620
ggaccttgc ctcccgcctg gacgtcttgt tggctcttgc cagtgctgcc cgggactacg  1680
gctattcgag accgcattac tctccctgta tccatggagt acgaatcagg aatggcaggc  1740
atcctctgat ggaactgtgt gcacgaacct tcgtgcccaa ctccacggac tgtggtgggg  1800
accagggcag ggtcaaagtc atcactggac ccaactcctc agggaaaagc atatatctca  1860
agcaggtagg cttgatcact ttcatggccc tggtgggcag tttcgtgcct gcagaggagg  1920
ccgagattgg ggtaatcgac gccatcttca ctcgaattca cagctgcgaa tccatctccc  1980
tcggcctctc caccttcatg attgatctca accaggtggc gaaagcagtg aacaatgcca  2040
cagagcactc gctggtcctg atcgatgaat tcgggaaggg gaccaactcg gtggatggcc  2100
tggcacttct ggctgctgtg ctccgtcact ggcttgcact gggacccagc tgccccacg   2160
tctttgtagc caccaacttc ctgagccttg ttcagctgca gctgctgccg caaggacccc  2220
tggtgcagta tttgaccatg gagacttgtg aggatgggga agaccttgtc ttcttctacc  2280
agctttgcca aggcgtcgcc agtgccagcc acgcctccca cacagcggcc caggctgggc  2340
ttcctgaccc actcattgct cgtggcaaag aggtctcaga cttgatccgc agtgggaaac  2400
```

```
ccatcaaggc cacgaatgag cttctaagga gaaaccaaat ggaaaactgc caggcactgg      2460
tggataagtt tctaaaactg gacttggagg atcccaccct ggacctggac attttcatta      2520
gtcaggaagt gctgcccgct gctcccacca tcctctgaga gtccttccag tgtcct          2576
```

<210> SEQ ID NO 54
<211> LENGTH: 833
<212> TYPE: PRT
<213> ORGANISM: Human

<400> SEQUENCE: 54

```
Met Ala Phe Arg Ala Thr Pro Gly Arg Thr Pro Pro Gly Pro Gly Pro
 1               5                  10                  15

Arg Ser Gly Ile Pro Ser Ala Ser Phe Pro Ser Pro Gln Pro Pro Met
                20                  25                  30

Ala Gly Pro Gly Gly Ile Glu Glu Asp Glu Glu Pro Ala Glu
            35                  40                  45

Ile His Leu Cys Val Leu Trp Ser Ser Gly Tyr Leu Gly Ile Ala Tyr
        50                  55                  60

Tyr Asp Thr Ser Asp Ser Thr Ile His Phe Met Pro Asp Ala Pro Asp
 65                  70                  75                  80

His Glu Ser Leu Lys Leu Leu Gln Arg Val Leu Asp Glu Ile Asn Pro
                85                  90                  95

Gln Ser Val Val Thr Ser Ala Lys Gln Asp Glu Ala Met Thr Arg Phe
            100                 105                 110

Leu Gly Lys Leu Ala Ser Glu Glu His Arg Glu Pro Lys Gly Pro Glu
        115                 120                 125

Ile Ile Leu Leu Pro Ser Val Asp Phe Gly Pro Glu Ile Ser Lys Gln
    130                 135                 140

Arg Leu Leu Ser Gly Asn Tyr Ser Phe Ile Ser Asp Ser Met Thr Ala
145                 150                 155                 160

Thr Glu Lys Ile Leu Phe Leu Ser Ser Ile Ile Pro Phe Asp Cys Val
                165                 170                 175

Leu Thr Val Arg Ala Leu Gly Gly Leu Leu Lys Phe Leu Ser Arg Arg
            180                 185                 190

Arg Ile Gly Val Glu Leu Glu Asp Tyr Asp Val Gly Val Pro Ile Leu
        195                 200                 205

Gly Phe Lys Lys Phe Val Leu Thr His Leu Val Ser Ile Asp Gln Asp
    210                 215                 220

Thr Tyr Ser Val Leu Gln Ile Phe Lys Ser Glu Ser His Pro Ser Val
225                 230                 235                 240

Tyr Lys Val Ala Ser Gly Leu Lys Glu Gly Leu Ser Leu Phe Gly Ile
                245                 250                 255

Leu Asn Arg Cys Arg Cys Lys Trp Gly Gln Lys Leu Leu Arg Leu Trp
            260                 265                 270

Phe Thr Arg Pro Thr Arg Glu Leu Arg Glu Leu Asn Ser Arg Leu Asp
        275                 280                 285

Val Ile Gln Phe Phe Leu Met Pro Gln Asn Leu Asp Met Ala Gln Met
    290                 295                 300

Leu His Arg Leu Leu Ser His Ile Lys Asn Val Pro Leu Ile Leu Lys
305                 310                 315                 320

Arg Met Lys Leu Ser His Thr Lys Val Ser Asp Trp Gln Val Leu Tyr
                325                 330                 335

Lys Thr Val Tyr Ser Ala Leu Gly Leu Arg Asp Ala Cys Arg Ser Leu
            340                 345                 350
```

-continued

```
Pro Gln Ser Ile Gln Leu Phe Gln Asp Ile Ala Gln Glu Phe Ser Asp
        355                 360                 365

Asp Leu His His Ile Ala Ser Leu Ile Gly Lys Val Val Asp Phe Glu
    370                 375                 380

Glu Ser Leu Ala Glu Asn Arg Phe Thr Val Leu Pro Asn Ile Asp Pro
385                 390                 395                 400

Asp Ile Asp Ala Lys Lys Arg Arg Leu Ile Gly Leu Pro Ser Phe Leu
                405                 410                 415

Thr Glu Val Ala Gln Lys Glu Leu Glu Asn Leu Asp Ser Arg Ile Pro
            420                 425                 430

Ser Cys Ser Val Ile Tyr Ile Pro Leu Ile Gly Phe Leu Leu Ser Ile
        435                 440                 445

Pro Arg Leu Pro Phe Met Val Glu Ala Ser Asp Phe Glu Ile Glu Gly
    450                 455                 460

Leu Asp Phe Met Phe Leu Ser Glu Asp Lys Leu His Tyr Arg Ser Ala
465                 470                 475                 480

Arg Thr Lys Glu Leu Asp Thr Leu Leu Gly Asp Leu His Cys Glu Ile
                485                 490                 495

Arg Asp Gln Glu Thr Leu Leu Met Tyr Gln Leu Gln Cys Gln Val Leu
            500                 505                 510

Ala Arg Ala Ser Val Leu Thr Arg Val Leu Asp Leu Ala Ser Arg Leu
        515                 520                 525

Asp Val Leu Leu Ala Leu Ala Ser Ala Ala Arg Asp Tyr Gly Tyr Ser
    530                 535                 540

Arg Pro His Tyr Ser Pro Cys Ile His Gly Val Arg Ile Arg Asn Gly
545                 550                 555                 560

Arg His Pro Leu Met Glu Leu Cys Ala Arg Thr Phe Val Pro Asn Ser
                565                 570                 575

Thr Asp Cys Gly Gly Asp Gln Gly Arg Val Lys Val Ile Thr Gly Pro
            580                 585                 590

Asn Ser Ser Gly Lys Ser Ile Tyr Leu Lys Gln Val Gly Leu Ile Thr
        595                 600                 605

Phe Met Ala Leu Val Gly Ser Phe Val Pro Ala Glu Glu Ala Glu Ile
    610                 615                 620

Gly Val Ile Asp Ala Ile Phe Thr Arg Ile His Ser Cys Glu Ser Ile
625                 630                 635                 640

Ser Leu Gly Leu Ser Thr Phe Met Ile Asp Leu Asn Gln Val Ala Lys
                645                 650                 655

Ala Val Asn Asn Ala Thr Glu His Ser Leu Val Leu Ile Asp Glu Phe
            660                 665                 670

Gly Lys Gly Thr Asn Ser Val Asp Gly Leu Ala Leu Ala Ala Val
        675                 680                 685

Leu Arg His Trp Leu Ala Leu Gly Pro Ser Cys Pro His Val Phe Val
    690                 695                 700

Ala Thr Asn Phe Leu Ser Leu Val Gln Leu Gln Leu Leu Pro Gln Gly
705                 710                 715                 720

Pro Leu Val Gln Tyr Leu Thr Met Glu Thr Cys Glu Asp Gly Glu Asp
                725                 730                 735

Leu Val Phe Phe Tyr Gln Leu Cys Gln Gly Val Ala Ser Ala Ser His
            740                 745                 750

Ala Ser His Thr Ala Ala Gln Ala Gly Leu Pro Asp Pro Leu Ile Ala
        755                 760                 765
```

```
Arg Gly Lys Glu Val Ser Asp Leu Ile Arg Ser Gly Lys Pro Ile Lys
        770                 775                 780
Ala Thr Asn Glu Leu Leu Arg Arg Asn Gln Met Glu Asn Cys Gln Ala
785                 790                 795                 800
Leu Val Asp Lys Phe Leu Lys Leu Asp Leu Glu Asp Pro Thr Leu Asp
                805                 810                 815
Leu Asp Ile Phe Ile Ser Gln Glu Val Leu Pro Ala Ala Pro Thr Ile
                820                 825                 830
Leu

<210> SEQ ID NO 55
<211> LENGTH: 232
<212> TYPE: DNA
<213> ORGANISM: Human

<400> SEQUENCE: 55
gtaacctccg cgtgacagaa tgagggtggg gcgcgtggag tttcccacaa tctgtacttt     60
agttaaatac ccgagaattc acctcctgtg tccacagctc tccacgcccc tcagccctgc    120
cccgcagccc tgtatcagaa gtacttagcg ctttgcattc tgcgcgccac cctaccccgg    180
cctcctctgt gaatcgttgc ttccgaaccg ccctcacttt ttgcatccgc ag            232

<210> SEQ ID NO 56
<211> LENGTH: 74
<212> TYPE: DNA
<213> ORGANISM: Human
<220> FEATURE:
<221> NAME/KEY: intron
<222> LOCATION: (73)..(74)
<223> OTHER INFORMATION: N = A or T or G or C

<400> SEQUENCE: 56
gtctctgagg ggagtagaaa cttgaatgga gagttgatgg gaatttaaaa taaagagggg    60
ttgggagccg ggnn                                                      74

<210> SEQ ID NO 57
<211> LENGTH: 189
<212> TYPE: DNA
<213> ORGANISM: Human

<400> SEQUENCE: 57
aaaaaaaaac agggttggga agagctgggc aagtctctta cctcctgagt ggctgtttca     60
cattcactaa atgggggtga tgatgccttat ctcagagatt tgagaaaatg attaaattat   120
ataagacatg gtaaacccta cacttatgag tgattctaat agtgatttcc tttcttcctt   180
gctggacag                                                            189

<210> SEQ ID NO 58
<211> LENGTH: 450
<212> TYPE: DNA
<213> ORGANISM: Human
<220> FEATURE:
<221> NAME/KEY: intron
<222> LOCATION: (449)..(450)
<223> OTHER INFORMATION: N = A or T or G or C

<400> SEQUENCE: 58
gtggggatgg aaccatgaat tcctctgctc tctgggattg cagatgtgtt acacacacac     60
acacacacac acacacacac acacatatat ttttttttc tagacagagt cttgctctgt    120
tacccaggct caagtgcagt ggcgcaatct tggctcactg cagcctccac ctcctgggtt   180
caagcaattc tcctgactca acctcccgag tagctggac tacaggcgtg tgccaccaca    240
cccagctagt ttttgtgtg tgtttttagc acagacggtg tttcaccatg ttggccaggg   300
```

```
tggtctcaaa ctcctgacct tgtgatccgc ccaccttggc ctcctaaagt gctgggacta      360
caggtgtgag tcaccacgcc cagccatgtt ttacttacat taactcacct cactgtctag      420
catattttgt gttgctgtaa ggaaatacnn                                        450
```

<210> SEQ ID NO 59
<211> LENGTH: 323
<212> TYPE: DNA
<213> ORGANISM: Human

<400> SEQUENCE: 59

```
ggcgacaaat atatatgacg tatttacaat gtttcaggtg cttcagattc agccctgggc       60
aaatcagtca tgtctgttct ccaggggttt acagcctagt gacaacatcc agaacatccc      120
acttccctct caccatccca ccactcttaa ctacttttct aaatctcaac ttctacctgt      180
gttcccactg tgcagagcac tccctactcc tagggaggaa atgttttttga gaaggagagg     240
ggtaggaaga ggagggctat gggttttctc ttagtcaaag acaaagatcc tttaactcat      300
ttgatctctg ttctccttcc aag                                              323
```

<210> SEQ ID NO 60
<211> LENGTH: 150
<212> TYPE: DNA
<213> ORGANISM: Human

<400> SEQUENCE: 60

```
gtaaggactt ggtaaaggat agagggaaaa tggggaagga ctaatatatg gaatattcca       60
gggggctaga attgggtgag agggagtgtc agacagaggt agaaggactg agatgtaaag      120
aatgatagcc ttttctttcc tcccccacag                                       150
```

<210> SEQ ID NO 61
<211> LENGTH: 733
<212> TYPE: DNA
<213> ORGANISM: Human

<400> SEQUENCE: 61

```
gtatctcctt cctttttgctt tgcctaactc cctgttccgg tgtcccattc tttcccccaa       60
ctctaccttc atcatcacag atctcccctc tgccttatgt catcctaaac ctttgtgctc      120
ctcatgccct atgacctgtc cccccaagat ctctcctgct ccctacccctt taataatctg     180
cagcttattg ggaagcctct gcttaagtca tgtctaggga tgagggcctc ccctgaggag      240
tggtgacact ttttggacag ggttttattg ttggaattct ccccattaag ttaaagcctt      300
ttatcaccaa accaaaaggc actgcctcag tgacccttat tatgatccat aaggcacttc      360
tataactttc ctaggtttac aataagaaca ggagtgtact atcctaatta gatattaagg      420
cattagtgtt actagttcta ttaataccat tattttgacc aaaatcctca attccagaca      480
gatgtctact ttcctcagcc atttatcttt ctcaggctgt gctttcagac aagtatcttt      540
atattatatg tagaataaaa agagaattag actaagagtc tgaaaatttg gttcttgctc      600
tagctttcca ttaactgcct gtgtgagctt gggcaagtca ataatctct cttgcttcta       660
ttgtctcatt cttaaaatgg ggtgaaaaaa ttgagctaca agaccgttcc ctttgcttgc      720
ctccctcaaa tag                                                         733
```

<210> SEQ ID NO 62
<211> LENGTH: 164
<212> TYPE: DNA
<213> ORGANISM: Human

<400> SEQUENCE: 62

```
gtgagattgg tcctggggga taagggctgg gaggcggcac aagtgctagg gctgaattct      60
gggaggtact ggcctagccc tggaaaatag taactttccc tggtgctctg cagcccccag     120
gagatttaag atttaccccg attccactgc tgatcccctc ccag                      164

<210> SEQ ID NO 63
<211> LENGTH: 246
<212> TYPE: DNA
<213> ORGANISM: Human

<400> SEQUENCE: 63
gtaggtgatt caccccaacc ccaaccaaag taatgtggga ttgggaggcc tgaaaagtaa      60
agtgggggtg gggtgtggat gtggctgtga cccagtgggt caagggctct aggacacccg     120
ggagaatcta agggctaatg agactttggg aagaagactg gacaatatt cagagagggg     180 gacaaaggaa gtggagttgt ggaacgaact cagactgctt cctgcttttt tgttttctgt    240
cctcag                                                                246

<210> SEQ ID NO 64
<211> LENGTH: 413
<212> TYPE: DNA
<213> ORGANISM: Human
<220> FEATURE:
<221> NAME/KEY: intron
<222> LOCATION: (412)..(413)
<223> OTHER INFORMATION: N = A or T or G or C

<400> SEQUENCE: 64
gtaaagaggt ggaggcatgc tgctgtctct ggggagggag aaggattaag tttaatgccc      60
caataatcct aatgaggctc tagtttccct aatcctgggg ctattaagat ctctctcctt    120
gaaggaaagg aagggggt tttgagggaa agagaggaag aaaagcataa agatactagc      180
tttcttttct ataggagaa actgaggcaa agaaaagtaa gggacaaacc ttacatcaag     240
atatgatctc ggctgggcgc ggtggctcat gcctgtaatc ccgcgctttg ggaggccaa     300 ggcgggtgga tcgcctgagg tcaggagttt gagacctgac caatatggta aaacccgtc    360 tctactaaaa atataaaaat tagctgggtg tgttgtgcgc ctgtaatccc ann           413

<210> SEQ ID NO 65
<211> LENGTH: 136
<212> TYPE: DNA
<213> ORGANISM: Human

<400> SEQUENCE: 65 tttttttta aaaaaaaaa aaaaagacg tgatctcagg aggatatccc ctgtccccat        60
tccatttatc agtcctcaat tcttattccc ctcaaaagtc caagttaccc caaactcctc   120
catttctcct cgacag                                                    136

<210> SEQ ID NO 66
<211> LENGTH: 356
<212> TYPE: DNA
<213> ORGANISM: Human
<220> FEATURE:
<221> NAME/KEY: intron
<222> LOCATION: (355)..(356)
<223> OTHER INFORMATION: N = A or T or G or C

<400> SEQUENCE: 66
gtaggtgtgc cccatccctc atctcacgta caaagaccta ccagaaaagc aattggctcc     60
```

```
aaagatgtgt cccagcctcc cttcccactt cactcccatt gtcagatatc tctttcatgc    120
caatccaaat ttcttaccta tttgtacccc ccgcccccca agcttgagca tcttcccata    180
ctttgtggct gtacagtgtg ttgcatatca gccattactt taccaattct gtgttccttc    240
cctgggtttg tatgaatgtt tctactagtt gggtacctgt tagggacttt gggagacctt    300
gtgtatagag aagagttttg taactgcata actgcctatt tgatttgtat agagnn        356

<210> SEQ ID NO 67
<211> LENGTH: 426
<212> TYPE: DNA
<213> ORGANISM: Human

<400> SEQUENCE: 67
ccaggagtag agggagagac agaaacagcc aacaatggcc cagaaaatgg atgatatatt     60
agataaggga gaaatgagt taccagattg gggagagatg gtttggatgt caaagcaggt    120
gatcggtgac gtcagcgtcc gagggaagac ggctgccacc ggcggggcca gttgagggaa    180
ctaggtagtt aagtgttgtc gggctaaaag tccctagagt gtccatccct cccccatctc    240
catgtgcggt aatcccagct catttagggg ccaggcacca actttggttg cctttgtgcc    300
ctcccaggcc agcttcctca acaaccagca cctctgactg gatgcctcag gttagacaca    360
taaacacatt ccattgccct gtccgtgcct tgtaacaagt tcactccctg ccttatccct    420
cacaag                                                               426

<210> SEQ ID NO 68
<211> LENGTH: 360
<212> TYPE: DNA
<213> ORGANISM: Human
<220> FEATURE:
<221> NAME/KEY: intron
<222> LOCATION: (359)..(360)
<223> OTHER INFORMATION: N = A or T or G or C

<400> SEQUENCE: 68
gtgagtgggt cccacacata ctacacacta atgcatgaat tccatatgca cactacatac     60
taagcctact aatggcagta tacagattct cacatacacc accccaccta gtagtagtaa    120
agcaactgcc ctttactgag cactggctaa ctgcatttca tccttataac agctttgtgt    180
agtagctgat atgcatctca ttttttgttg tcagcgcagg tacacatata cattgatgat    240
acacagactt gcacacatac agcagcagga aaaaacacaa aatgtaaggc cgggcacagt    300
ggctcacacc tgttatcagc actttggggg gccaacgctg ggtgaccttc catctttgnn    360

<210> SEQ ID NO 69
<211> LENGTH: 447
<212> TYPE: DNA
<213> ORGANISM: Human

<400> SEQUENCE: 69
cacaggaaga atatgaaaag atgaatgtct gttgctgtta cccagagaca ctttcacagc     60
taaaaagaca tacaaactca tactgactca ccgtctctta ctcagcctca gagtgagctg    120
cagtgttggc acacaaatac ctcaacacac tgctctcctt ctaaaatatt gacaagctcc    180
gttacttata tacatggaat gacacacggt cttatccgtt gaaactgtga tatgtagaca    240
caattatgct cacatctagc aattttcagt agatacatgt aaacacacct gaatgggtag    300
gacactgcac ttgccactac attcccatag cacatcgtgg atacatattg ccacaatccc    360
cagggactgc aagcacactt tttggcaaac tgagatcaag atgatagatg taacttgtag    420
```

```
tacccccacc caaaccctca cttccag                                          447

<210> SEQ ID NO 70
<211> LENGTH: 127
<212> TYPE: DNA
<213> ORGANISM: Human

<400> SEQUENCE: 70
gtgagcccag ggtggagggc agggaggtgg ggaaggaggt tgagggctga tactgggcag       60
tgggcttctt gagggggcatt agagtgaggg aagagaaaac agcggctgta accttgtctg     120
actgtag                                                                127

<210> SEQ ID NO 71
<211> LENGTH: 30
<212> TYPE: DNA
<213> ORGANISM: Human
<220> FEATURE:
<221> NAME/KEY: intron
<222> LOCATION: (29)..(30)
<223> OTHER INFORMATION: N = A or T or G or C

<400> SEQUENCE: 71
gtaaggcctt ccttcttgaa tcccaaaann                                        30

<210> SEQ ID NO 72
<211> LENGTH: 222
<212> TYPE: DNA
<213> ORGANISM: Human

<400> SEQUENCE: 72
tacaggcatg agccactgtg cctggccagg accatatctt aattgtcttt gtagtttcag       60
tgtttggtac agtgcctctc actgtttctt tttgcctttg agatcttccc tctttgttac     120
tgtgatcttc cctactggtc tttgttcttc tgagtctgtc cctatcacca cctcaacccg     180
agctggatgt ggcctgtcct ccttttttgtg tttctctcac ag                        222

<210> SEQ ID NO 73
<211> LENGTH: 254
<212> TYPE: DNA
<213> ORGANISM: Human

<400> SEQUENCE: 73
gtgagtagaa ggaaaaaggg agtgcaccca gggaggtcag ggagagagaa tgcagtgtgc       60
aagatgggga acatggaag atattgaggt caattggata agaatggga tggtgggagg      120 aggcagcaga acttcaggga agtatctgga gggtgagagt taaggagga ctgcagggag     180 aattggggcc caaggagagc tgaggaacag dacagagggt gccaggtcct aagaaacagt    240
acttatctcc tcag                                                        254

<210> SEQ ID NO 74
<211> LENGTH: 145
<212> TYPE: DNA
<213> ORGANISM: Human

<400> SEQUENCE: 74
gtgagtgttg ggtgtggatg ggcctgtgag ccctgcgcag tgatggagta ccatccttgg       60
caggtggtca ccacagctgg ggatcttcat agcaaccagg gcaggagact cacttttgat     120
aaccacctgt cttccacccct cgtag                                           145
```

```
<210> SEQ ID NO 75
<211> LENGTH: 98
<212> TYPE: DNA
<213> ORGANISM: Human
<220> FEATURE:
<221> NAME/KEY: intron
<222> LOCATION: (97)..(98)
<223> OTHER INFORMATION: N = A or T or G or C

<400> SEQUENCE: 75
gtgagggcag gagagtgggt gtagccttca gatgtctttt gggggagata ttaggcttat      60
gaaagacata ctggtagata agaaaacttg tggggcnn                             98

<210> SEQ ID NO 76
<211> LENGTH: 83
<212> TYPE: DNA
<213> ORGANISM: Human

<400> SEQUENCE: 76
atcttttaag ctcccttggg atggggaggt tccagtaagt ctccaaacaa gagagtagag      60
tatctcctct ttactctccc cag                                              83

<210> SEQ ID NO 77
<211> LENGTH: 247
<212> TYPE: DNA
<213> ORGANISM: Human

<400> SEQUENCE: 77
gtaagaccct caacctctgt aaggtgagtg atgaggaaaa tgagtcagca gctgaggaag      60
agcgttactc tacagcagca ctgcccaata tgggatctct cctctgtagt tttactctga     120
gctttaccag cactgagaca aaggaaagag aagtcagagt taggggctgg aggtgggggtt    180 agaaagatgg ggaaggagag gaggaccaag agatgcaaag tccacagctt tgaacccctg     240
tacccag                                                                247

<210> SEQ ID NO 78
<211> LENGTH: 273
<212> TYPE: DNA
<213> ORGANISM: Human

<400> SEQUENCE: 78
gtgaggaaaa gccagaggtt atatgcattg taagatgttt aaaaaaagca gcagccaggg      60
gaaggagggg agtgggcaac ttggggatgc ttccaacagg cccctcctct tcctgctctc     120
tgtctcgctc actctgactc tatcttttcc tctgaatgtc ttgaggtctc agattgtatc     180
tgcaacctgt ttccagatcc ccctagggge ctctgcctct ccttcacttt ccctggaac      240 tgacctccag ctcccttcct cacccactcc cag                                   273

<210> SEQ ID NO 79
<211> LENGTH: 114
<212> TYPE: DNA
<213> ORGANISM: Human

<400> SEQUENCE: 79
gtaagaatag aggcgggtgg aggaatacac atgaggggcc caaaggctac atcttctggg      60
ggttcatcta tcttgatcca caagccatgc gaggtgcctc tccgcccact gcag           114

<210> SEQ ID NO 80
<211> LENGTH: 473
```

```
<212> TYPE: DNA
<213> ORGANISM: Human

<400> SEQUENCE: 80
gtgaggagaa gccctgcagc ctgggcctct ggcgtctcct gcatctactc caccccctact    60
tgccagccaa ctcaggctcc tgcagctctt ctcccatttt ctgaccccgc tcttcatgaa   120
aggaccatca cccacatccc tgtgcttcca cctcacatgt tcttattctc cactggagag   180
ccatgctcta atggaacttt ccgtggccca aattccttca cctgcctctg agtaggtaca   240
caccactccc aagtatgtct ctgcccacgt cccgtgcctc ttcactgatt ctaaattagc   300
ccacagggct atggtcagga ttcggggagg agagacagag tcagtgtgtc tgttacctat   360
ttctcctgtt tcaccctgtc catttctctt tgatgtgcca ttcatgcctt gagcctcact   420
ttcacctcag cccacggcac caggccccag gccctgtctc cttccctatt cag          473

<210> SEQ ID NO 81
<211> LENGTH: 348
<212> TYPE: DNA
<213> ORGANISM: Human

<400> SEQUENCE: 81
gtcaaaggga acaaagggag gtgggattga ggaaggggat aatgggaaag gaaccctga     60
aaatgctcat aacaggaaag catgccctct gctgcatgcc ctttatacta aagtgggga   120
gcactaaggt cagagataag aagaatcaat accataaaca tttcttgaac ccttgtttca   180
tgtgagtcac tgttggcaaa gaggatgaac aaagcgtgca cctcaccatt caagaacttg   240
cagtgcagta gggagggcat gtatacagct ttattcacag ccaactgtg gtcagtgcgt    300
tacgggcttc caatactaac ttccccttgt ccaccttata cccagcag                348

<210> SEQ ID NO 82
<211> LENGTH: 209
<212> TYPE: DNA
<213> ORGANISM: Human

<400> SEQUENCE: 82
gtgaggggag aaactgatga ggggagaaac taaggagggg aaaatggagg aggatgaagg    60
agcatgacag tgaggctggg cctctggaat ggaatagggc tgtgtgggca gaaaagaaat   120
agaacacgag acagggaaag gcagtgcaag tgcagagggg catatggggt ccccatggct   180
ccgaatgcta acctctgccc tctttgcag                                      209

<210> SEQ ID NO 83
<211> LENGTH: 202
<212> TYPE: DNA
<213> ORGANISM: Human

<400> SEQUENCE: 83
gtgaggagac caatctagct cctcggggac ccccaggctg ggcatttccc agaggtgggg    60
attggctcct ctatcagaac aagggctccc tcagcacaga gaccacatcc cttcccttt   120
ctccctcccc acaggattgg ccaagggttt caggacagga aggaggtgat tgatgataca   180
ctgtcttta ttctcttta ag                                               202

<210> SEQ ID NO 84
<211> LENGTH: 155
<212> TYPE: DNA
<213> ORGANISM: Human
```

```
<400> SEQUENCE: 84
gtgatgagat ccaaatgtgc aaccacctcc acatcagagc tcccttcat tcctagtcct      60 actgggcctg ggtctaggtc cacaggattt ctgacccta tttccccttc tcttccccac    120
tccccttact cctcccacct tcttgcttgt cctag                                155

<210> SEQ ID NO 85
<211> LENGTH: 215
<212> TYPE: DNA
<213> ORGANISM: Human

<400> SEQUENCE: 85
gtgcgtatat ggccccagtg tctttaccct ctctgcatct tctcctgcaa ctcttctccc     60
ccctccagca ctttgccctt cagaaaccca ccatttcttt ctgaaatccc taaatcttca   120
agatcccagg ttttctgtgc cacagcctct ccctctgcc cagggatttg gttgtccatt    180
ctgccataaa tcttgcgatt ttctctcttc ttcag                               215

<210> SEQ ID NO 86
<211> LENGTH: 29
<212> TYPE: DNA
<213> ORGANISM: Human

<400> SEQUENCE: 86
gctgctcagg tatacagtac cacgctccc                                       29

<210> SEQ ID NO 87
<211> LENGTH: 29
<212> TYPE: DNA
<213> ORGANISM: Human

<400> SEQUENCE: 87
agatccgggg tgaggagccc gtggtagga                                       29

<210> SEQ ID NO 88
<211> LENGTH: 29
<212> TYPE: DNA
<213> ORGANISM: Human

<400> SEQUENCE: 88
gaatggcagg tgagaagggg ccccatgtc                                       29

<210> SEQ ID NO 89
<211> LENGTH: 29
<212> TYPE: DNA
<213> ORGANISM: Human

<400> SEQUENCE: 89
ctcaagcagg tgagggggccg ccaagctgg                                      29

<210> SEQ ID NO 90
<211> LENGTH: 29
<212> TYPE: DNA
<213> ORGANISM: Human

<400> SEQUENCE: 90
accaactcgg tgcggaggaa aatgaagag                                       29

<210> SEQ ID NO 91
<211> LENGTH: 29
<212> TYPE: DNA
<213> ORGANISM: Human
```

<400> SEQUENCE: 91
ttcccatccc aaccctccag gctgtggtt                                              29

<210> SEQ ID NO 92
<211> LENGTH: 29
<212> TYPE: DNA
<213> ORGANISM: Human

<400> SEQUENCE: 92
ctctctctct ccttctccag accaggaga                                              29

<210> SEQ ID NO 93
<211> LENGTH: 29
<212> TYPE: DNA
<213> ORGANISM: Human

<400> SEQUENCE: 93
tgtctctcta cccaccacag gcatcctct                                              29

<210> SEQ ID NO 94
<211> LENGTH: 29
<212> TYPE: DNA
<213> ORGANISM: Human

<400> SEQUENCE: 94 tctccctgc cctggcccag gtaggcttg                                               29

<210> SEQ ID NO 95
<211> LENGTH: 29
<212> TYPE: DNA
<213> ORGANISM: Human

<400> SEQUENCE: 95
tcacctctgc cctttgacag gtggatggc                                              29

<210> SEQ ID NO 96
<211> LENGTH: 79
<212> TYPE: DNA
<213> ORGANISM: Human

<400> SEQUENCE: 96
gtatacagta ccacgctccc caagcaaagt caagatgaga gaagacgtga cttgtaacct           60
tcccatccca accctccag                                                        79

<210> SEQ ID NO 97
<211> LENGTH: 135
<212> TYPE: DNA
<213> ORGANISM: Human

<400> SEQUENCE: 97
gtgaggagcc cgtggtagga gggggcaggc tgctctaaca gaccctgctc tcatgctggc           60
ccctctgcat ggtcacactg catctgcatg cctgcttcca gatctttcca ggcacctctc          120
tctctccttc tccag                                                           135

<210> SEQ ID NO 98
<211> LENGTH: 79
<212> TYPE: DNA
<213> ORGANISM: Human

<400> SEQUENCE: 98

-continued

```
gtgagaaggg gccccatgtc ctgctgtggg gatcctccct gggtccacaa accatgcagt    60
gtctctctac ccaccacag                                                 79
```

<210> SEQ ID NO 99
<211> LENGTH: 389
<212> TYPE: DNA
<213> ORGANISM: Human

<400> SEQUENCE: 99

```
gtgaggggcc gccaagctgg gggcccacat ctccatctcc tctggccgcc aggccagatc    60
ctctgccccc ccccacacac acatacagca catgtccttg tcctctgagg acagtctgt    120 tctttaggat agacctttcc gtggccacaa gtccctggac caactcccaa atagatccat   180
gccgttccct agtatgcctt taccacaac cttgactctg gagttaattg tgaagtcagg    240
acccaggaaa ctgtgttcca gggtctgtt cttctgttac actgtgtcct ctctttaatc    300
tgtcgttcat gtctttagtt gagacccatt tttactttgc ccatagtacg gcaacaggcc   360
catgttctgt ctccctgcc ctggcccag                                      389
```

<210> SEQ ID NO 100
<211> LENGTH: 180
<212> TYPE: DNA
<213> ORGANISM: Human

<400> SEQUENCE: 100

```
gtgcggagga aaatgaagag atgctaagga gggggatgg aggaaaatga gaaccgggag    60
caggagactg acctcaggga agaaaagggg gatgcgtgca cagaggggag gagaagccat   120
gacagctaca gaaggacaca gctgtcctgg ttctgccctc tcacctctgc cctttgacag   180
```

<210> SEQ ID NO 101
<211> LENGTH: 20
<212> TYPE: DNA
<213> ORGANISM: Human

<400> SEQUENCE: 101

```
ccagaactct ctggagaagc                                                20
```

<210> SEQ ID NO 102
<211> LENGTH: 21
<212> TYPE: DNA
<213> ORGANISM: Human

<400> SEQUENCE: 102

```
gtgctgtgga attcaggata c                                              21
```

<210> SEQ ID NO 103
<211> LENGTH: 27
<212> TYPE: DNA
<213> ORGANISM: Human

<400> SEQUENCE: 103

```
ctccactatc cacttcatgc cagatgc                                        27
```

<210> SEQ ID NO 104
<211> LENGTH: 28

```
-continued
<212> TYPE: DNA
<213> ORGANISM: Human

<400> SEQUENCE: 104
gctggggagg acactggaag gactctca                                            28
```

METHOD OF DETECTION OF ALTERATIONS IN MSH5

CROSS-REFERENCE TO RELATED APPLICATIONS

This application is a divisional under 35 U.S.C. § 120 of application Ser. No. 09/470,276, filed Dec. 22, 1999, now U.S. Pat. No. 6,670,460 which is a continuation under 35 U.S.C. § 120 of application No. PCT/US98/13850, filed Jul. 2, 1998, which claims the benefit under 35 U.S.C. § 119(e) of Provisional Application No. 60/051,686, filed Jul. 3, 1997.

FIELD OF THE INVENTION

The present invention pertains to a mammalian DNA mismatch repair gene, MSH5, and uses thereof, for example, in drug screening, cancer prognosis and diagnosis. The gene product is required for meiotic crossing over and segregation of chromosomes during meiosis. More specifically, the invention relates to detection of alterations in the gene which are associated with some mammalian, preferably human, cancers, as well as conditions involving problems in meiotic segregation.

BACKGROUND OF THE INVENTION

Accurate transmission of genetic information is important in the survival of a cell, an organism, and a species. A number of mechanisms have evolved that help to ensure high fidelity transmission of genetic material from one generation to the next since mutations can lead to new genotypes that may be deleterious to the cell. DNA lesions that frequently lead to mutations are modified, missing or mismatched nucleotides. Multiple enzymatic pathways have been described in prokaryotic systems that can specifically repair these lesions.

There are at least three ways in which mismatched nucleotides arise in DNA. First, physical damage to the DNA or DNA precursors can give rise to mismatched bases in DNA. For example, the deamination of 5-methyl-cytosine creates a thymine and, therefore, a G-T mispair. Second, misincorporation, insertion, or deletion of nucleotides during DNA replication can yield mismatched base pairs. Finally, genetic recombination produces regions of heteroduplex DNA which may contain mismatched nucleotides when such heteroduplexes result from the pairing of two different parental DNA sequences. Mismatched nucleotides produced by each of these mechanisms are known to be repaired by specific enzyme systems.

The well defined mismatch repair pathway is the *E. coli* MutHLS pathway that promotes a long-patch (approximately 3 Kb) excision repair reaction which is dependent on the muth, mutL, mutS and MutU (uvrD) gene products. The MutHLS pathway appears to be the most active mismatch repair pathway in *E. coli* and is known to both increase the fidelity of DNA replication and act on recombination intermediates containing mispaired bases. This system has been reconstituted in vitro and requires the MutH, MutL, MutS and UvrD (helicase II) proteins along with DNA polymerase III holoenzyme, DNA ligase, single-stranded DNA binding protein (SSB) and one of the single-stranded DNA exonucleases, Exo I, Exo VII or RecJ. MutS protein binds to the mismatched nucleotides in DNA. MutH protein interacts with GATC sites in DNA that are hemi-methylated on the A and is responsible for incision on the unmethylated strand. Specific excision of the unmethylated strand results in increased fidelity of replication because excision is targeted to the newly replicated unmethylated DNA strand. MutL facilitates the interaction between MutS bound to the mismatch and MutH bound to the hemi-methylated Dam site resulting in the activation of MutH. UvrD is the helicase that appears to act in conjunction with one of the single-stranded DNA specific exonucleases to excise the unmethylated strand leaving a gap which is repaired by the action of DNA polymerase III holoenzyme, SSB and DNA ligase. In addition, *E. coli* contains several short patch repair pathways including the VSP system and the MutY (MicA) system that act on specific single base mispairs.

In bacteria, therefore, mismatch repair plays a role in maintaining the genetic stability of DNA. The bacterial MutHLS system has been found to prevent genetic recombination between the divergent DNA sequences of related species such as *E. coli* and *S. typhimurium* (termed: homologous recombination).

A number of human mismatch repair genes have been discovered. Defects in the human MSH2 gene are associated with Hereditary Non-Polyposis Colon Cancer (HNPCC), a familiar form of human colorectal cancer (CRC) that is also known as Lynch's Syndrome. Other mismatch repair genes discovered in humans include MLH1.

These genes are not only involved with susceptibility to cancer, but can be associated with other aspects. For example, defects in MSH2 and MLH1 confer resistance to alkylating agents frequently used in treating cancers. Consequently, the discovery of mismatch repair genes is extremely important. For example, finding a new mismatch repair gene permits one to look for defects in that gene and determine its association with particular cancers. This not only permits one to determine susceptibility to particular cancers, but to have a better prognosis of the disease and to more fully understand what therapies to use. Thus, being able to find additional mammalian, particularly human, mismatch repair genes is very important.

SUMMARY OF THE INVENTION

We have discovered and sequenced mammalian MSH5 genes which are involved in the DNA mismatch repair pathway. We have identified its chromosomal location in humans as well as the intron-exon borders in both mice and humans. This gene produces a protein involved in meiotic crossing over and segregation of chromosomes during meiosis. Thus, defects in the gene should indicate susceptibility to disorders associated with those activities such as Downs Syndrome and certain types of infertility. Further defects in mismatch repair genes indicate susceptibility to various types of cancer. Moreover, defects in this gene confer resistance to alkylating agents. Alkylating agents represent a preferred class of chemotherapeutic agents frequently used in treating cancer.

Consequently, individuals diagnosed with cancer should have that cancer screened for the presence of a defect in the MSH5 gene. If the individual has such a defect, then an agent other than an alkylating agent should be prescribed. This gene, also has other applications. It can be used in assays, to express gene product, for drug screens, and therapeutically.

DESCRIPTION OF THE SEQUENCE LISTING

SEQ ID NO.:1 is the nucleotide sequence of the human MSH5 MSH2 gene.

SEQ ID NO.:2 is the deduced amino acid sequence of the human MSH5 gene product.

SEQ ID NOs.:3-26 are the nucleotide sequence of the 5'=exon-intron borders.

SEQ ID NOs:27-50 are the nucleotide sequences of the 3'=intron-exon borders.

SEQ ID NOs: 51 and 52 are primers used in screening for human genomic MSH5.

SEQ ID NO:53 is the nucleotide sequence of the murine MSH5 gene.

SEQ ID NO:54 is the deduced amino acid sequence of the murine MSH5 gene product.

SEQ ID NOs:55-85 represent nucleotide intronic sequences of human MSH5.

SEQ ID NOs:86-90 are nucleotide sequences of the 5' exon-intron borders of mMSH5.

SEQ ID NOs:91-95 are nucleotide sequences of the 3' intron-exon borders of mMSH5.

SEQ ID NOs:96-100 represent nucleotide intronic sequences of murine MSH5.

SEQ ID NOs:101-104 are primers used.

DETAILED DESCRIPTION OF THE INVENTION

We have discovered that mammals have a DNA mismatch repair gene analogous to a gene that exists in bacteria and yeast. Defects or alterations in this mismatch repair gene in a mammal, such as a human, will result in abnormalities in meiotic crossing over and segregation of chromosomes during meiosis. Such a phenotype should have a high correlation with abnormalities associated with such defects. For example, in many types of infertility and Downs Syndrome, problems in meiotic chromosome segregation are present. Accordingly, discovering a defect or alteration in the MSH5 gene (SEQ ID NO:1 provides the complete human sequence) can be diagnostic of a predisposition to such an abnormality. Additionally, mismatch repair genes are typically associated with an increased risk of cancer. Thus, the discovery of defects in MSH5 can be diagnostic of a predisposition to cancer, and prognostic for a particular cancer.

The diagnostic and prognostic methods of the present invention include looking for an alteration in mammalian MSH5 gene. Preferably, the mammalian MSH5 gene is human. The alteration may be due to a deletion, addition and/or mutation, such as a point mutation, in the gene. Any of these types of mutations can lead to non-functional gene products. The mutational events may occur not only in an exon, but also in an intron or non-exonic region. As a result of alterations of this kind, including alterations in non-exonic regions, effects can be seen in transcription and translation of members of the pathway, thereby affecting the ability to repair mismatch errors or meiotic events. The changes resulting from these alterations are also reflected in the resultant protein and mRNA as well as the gene. Other alterations that might exist in the pathway include changes that result in an increase or decrease in expression of a gene in the mismatch repair pathway.

Consequently, one aspect of this invention involves determining whether there is an alteration of MSH5. This determination can involve screening for alterations in the gene, its mRNA, its gene products, or by detecting other manifestations of defects in the pathway. Alterations can be detected by screening for a particular mismatch repair element in a suitable sample obtained, for example, from tissue, human biological fluid, such as blood, serum, plasma, urine, cerebrospinal fluid, supernatant from normal cell lysate, supernatant from preoplastic cell lysate, supernatant from neoplastic cell lysate, supernatants from carcinoma cell lines maintained in tissue culture, eukaryotic cells, etc.

In order to detect alterations in MSH5 from a particular tissue, such as a malignant tissue, it is helpful to isolate that tissue type free from the surrounding tissues. Means for enriching a tissue preparation e.g., for tumor cells, are known in the art. For example, the tissue may be isolated from paraffin or cryostat sections. Cancer cells may also be separated from normal cells by flow cytometry. These as well as other techniques for separating specific tissue types from other tissues, such as tumor from normal cells, are well known in the art. It is also helpful to screen normal tissue free from malignant tissue. Then comparisons can be made to determine whether a malignancy results from a spontaneous change in the mismatch repair pathway or is genetic.

Detection of mutations may be accomplished by molecular cloning of the MSH5 gene present in the tissue and sequencing the genes using techniques well known in the art. For example, mRNA can be isolated, reverse transcribed and the cDNA sequenced. Alternatively, the polymerase chain reaction can be used to amplify the MSH5 gene or fragments thereof directly from a genomic DNA preparation from the tissue such as tumor tissue. The DNA sequence of the amplified sequences can then be determined. Alternatively, one can screen for marker portions of the DNA that are indicative of changes in the DNA. The polymerase chain reaction itself is well known in the art. See e.g., Saiki et al., Science, 239:487 (1988); U.S. Pat. No. 4,683,203; and U.S. Pat. No. 4,683,195. Specific primers which can be used in order to amplify the mismatched repair genes will be discussed in more detail below.

Specific deletions of mismatch repair pathway genes can also be detected. For example, restriction fragment length polymorphism (RFLP) probes for the MSH5 gene or portion thereof, can be used to score loss of a wild-type allele. Other techniques for detecting deletions, as are known in the art, can be used.

Loss of the wild-type MSH5 may also be detected on the basis of the loss of a wild-type expression product. Such expression products include both the mRNA as well as the protein product itself. Point mutations may be detected by sequencing the mRNA directly or via molecular cloning of cDNA made from the mRNA. The sequence of the cloned cDNA can be determined using DNA sequencing techniques which are well known in the art. Alternatively, one can screen for changes in the protein. For example, a panel of antibodies, for example single chain or monoclonal antibodies, could be used in which specific epitopes involved in, for example, MSH5 meiotic segregation functions are represented by a particular antibody. Loss or perturbation of binding of a monoclonal antibody in the panel would indicate mutational alteration of the protein and thus of the gene itself. Alternatively, deletional mutations leading to expression of truncated proteins can be quickly detected using a sandwich type ELISA screening procedure, in which, for example, the capture antibody is specific for the N-terminal portion of the pathway protein. Failure of a labeled antibody to bind to the C-terminal portion of the protein provides an indication that the protein is truncated. Even where there is binding to the C-terminal, further tests on the protein can indicate changes. For example, molecular weight comparison. Any means for detecting altered mismatch repair pathway proteins can be used to detect loss of wild-type mismatch repair pathway genes.

Alternatively, mismatch detection can be used to detect point mutations in the MSH5 gene or its mRNA product. While these techniques are less sensitive than sequencing, they can be simpler to perform on a large number of cells. An example of a mismatch cleavage technique is the RNAase protection method, which is described in detail in Winter et al., Proc. Natl. Acad. Sci. USA, 82:7575 (1985) and Meyers et al., Science, 230:1242 (1985). In the practice of the present invention, the method involves the use of a labeled riboprobe which is complementary to the human wild-type MSH5. The riboprobe and either mRNA or DNA-isolated form the test tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mismatch repair pathway mRNA or DNA. The riboprobe comprises only a segment of the MSH5 mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Nat. Acad. Sci. USA, 85:4397 (1988); and Shenk et al., Proc. Natl. Acad. Sci. USA, 72:989 (1975). Alternatively, mismatches can be detected by shifts in the electrophoretic mobility of mismatched duplexes relative to matched duplexes. See, e.g., Cariello, Human Genetics, 42:726 (1988). With either riboprobes or DNA probes, the cellular mRNA or DNA which might contain a mutation can be amplified using PCR before hybridization.

DNA sequences of the MSH5 gene from test tissue which have been amplified by use of polymerase chain reaction may also be screened using allele-specific probes. These probes are nucleic acid oligomers, each of which contains a region of the MSH5 gene sequence harboring a known mutation. By use of a battery of allele-specific probes, the PCR amplification products can be screened to identify the presence of a previously identified mutation in the gene. Hybridization of allele-specific probes with amplified mismatch repair pathway sequences can be performed, for example, on a nylon filter. Hybridization to a particular probe indicates the presence of the same mutation in the tumor tissue as in the allele-specific probe.

Altered MSH5 gene or gene products can be detected in a wide range of biological samples, such as serum, stool, or other body fluids, such as urine and sputum. The same techniques discussed above can be applied to all biological samples. By screening such biological samples, a simple early diagnosis can be achieved for many types of abnormalities such as defects in chromosomal segregation or cancers. For example someone can be screened as part of a pre-pregnancy battery of tests. Thus, if fertility problems arise, the knowledge of the defect can be used in determining the treatment. Moreover, even if a pregnancy results, the knowledge can be used in determining whether and the types of pre-natal screening.

Similarly, even when someone has been diagnosed with cancer, these screens can be prognostic of the condition, e.g., spontaneous mutation versus hereditary. The prognostic method of the present invention is useful for clinicians so that they can decide upon an appropriate course of treatment. For example, a hereditary mutation in the DNA mismatch repair system suggests a different therapeutic regimen than a sporadic mutation. In addition, mutations in MSH5 confer resistance to alkylating agents which are frequently used in cancer chemotherapy. Thus, knowing of a defect permits one to choose an alternative course of therapy.

The methods of screening of the present invention are applicable to any sample in which defects in MSH5 has a role, such as in tumorigenesis.

The method of the present invention for diagnosis of, for example, a DNA mismatch repair defective tumor is applicable across a broad range of tumors. These include breast, lung, colorectal, ovary, endometrial (uterine), renal, bladder, skin, rectal and small bowel.

The present invention also provides a kit useful for determination of the nucleotide sequence of a MSH5 using a method of DNA amplification, e.g., the polymerase chain reaction or an antibody. The kit comprises a set of pairs of single stranded oligonucleotide DNA primers which can be annealed to sequences within or surrounding the MSH5 gene in order to prime amplifying DNA synthesis of the gene itself or to use as antibody for the gene product. In one preferred embodiment instructions for using the materials to screen for MSH5 for diagnosis or prognosis purposes are included.

In order to facilitate subsequence cloning of amplified sequences, primers may have restriction enzyme sites appended to their 5' ends. Thus, all nucleotides of the primers are derived from the mismatch repair gene sequences or sequences adjacent thereto except the few nucleotides necessary to form a restriction enzyme site. Such enzymes and sites are well known in the art. The primers themselves can be synthesized using techniques which are well known in the art. Generally, the primers can be made using synthesizing machines which are commercially available.

In a preferred embodiment, the set of primer pairs for detecting alterations in the hMSH5 gene comprises primer pairs that would border intron/exon borders. For example, one could use SEQ ID NOS:3-26 to pick one member of the pair and SEQ ID NOS:27-50 to pick another member. One can readily derive other primers to use based upon these sequences. Typically the primer will be at least about 10 nucleotides, more preferably at least about 13 nucleotides, still more preferably at least about 15 nucleotides, even more preferably at least about 20 nucleotides. Typical primer sizes will range from about 17 to 23 nucleotides.

According to the present invention, a method is also provided of supplying MSH5 function to a cell which carries a mutant gene. The wild-type MSH5 gene or a functional part of the gene such as a domain supplying a particular function may be introduced into the cell in a vector such that the gene remains extrachromosomal. In such a situation, the gene will be expressed by the cell from the extrachromosomal location. By using traditional deletion mutant analysis, specific functional domains can readily be determined. For example, a domain supplying meiotic function. Alternatively, one can select a domain that supplies mismatch repair function. If a gene portion is introduced and expressed in a cell carrying a mutant MSH5, the gene portion should encode a part which is defective or deficient in that cell. More preferred is the situation where the wild-type mismatch repair pathway gene or a part of it is introduced into the mutant cell in such a way that it recombines with the endogenous mutant MSH5 gene present in the cell. Such recombination would require stable integration into the cell such as via a double recombination event which would result in the correction of the gene mutation.

Vectors for introduction of genes both for recombination and for extrachromosomal maintenance are known in the art and any suitable vector may be used. Such a cell can be used in a wide range of activities. For example, one can prepare a drug screen using a tumor cell line having a defect in the mismatch repair pathway and by this technique create a control cell from that tumor cell. Thus, one can determine if the compounds tested affect the pathway. Such a method can be used to select drugs that specifically affect the pathway or as a screen for agents, including known anti-cancer agents, that are effective against mismatch repair defective tumors. These drugs may be combined with other drugs for their combined or synergistic effects. In contrast, when comparing normal cells with neoplastic cells there can be a variety of factors affecting such cells, thus, such a comparison does not provide the same data. These cells may also be able to be used therapeutically, for example, in somatic cell therapy, etc.

The present invention further provides a method for determining whether an alteration in a MSH5 gene is a mutation or an allelic variation. The method comprises introducing the altered gene into a cell having a mutation in the MSH5 gene being tested. The cell may be in vitro or in vivo. If the altered gene tested is an allelic variation, i.e., function is maintained, the mutation will be complemented and the cell will exhibit a wild-type phenotype. In contrast, if the altered gene in a mutation, the mutation will not be complemented and the cell will continue to exhibit non-wild type phenotype.

One can also prepare cell lines stably expressing MSH5. Such cells can be used for a variety of purposes including an excellent source of antigen for preparing a range of antibodies using techniques well known in the art.

Polypeptides or other molecules which have functional MSH5 activity may be supplied to cells which carry mutant alleles. The active molecules can be introduced into the cells by microinjection or by liposomes, for example. Alternatively, some such active molecules may be taken up by the cells, actively or by diffusion. Supply of such active molecules will effect a desired state, for example, meiotic segregation. Predisposition to a difficulty with appropriate segregation of chromosomes or to cancers can be ascertained by testing normal tissues of humans. For example, a person who has inherited a germline MSH5 alteration would be prone to develop one of these abnormalities, for example cancers. This can be determined by testing DNA or mRNA from any tissue of the person's body. Most simply, blood can be drawn and the DNA or mRNA extracted from cells of the blood. Loss of a wild-type MSH5 allele, either by point mutation, addition or by deletion, can be detected by any of the means discussed above. Nucleic acid can also be extracted and tested from fetal tissues for this purpose.

Accordingly, the present invention provides for a wide range of assays (both in vivo and in vitro). These assays can be used to detect cellular activities of the members in an MSH5 activity such as mismatch repair, which include eukaryotic nucleotide sequences that are homologous to bacterial or yeast MSH5 and the cellular activities of the polypeptides they encode. In these assay systems, MSH5 genes, polypeptides, unique fragments, or functional equivalents thereof, may be supplied to the system or produced within the system. For example, such assays could be used to determine whether there is a MSH5 gene excess or depletion. For example, an in vivo assay systems may be used to study the effects of increased or decreased levels of transcript or polypeptides of the invention in cell or tissue cultures, in whole animals, or in particular cells or tissues within whole animals or tissue culture systems, or over specified time intervals (including during embryogenesis).

Another aspect of the invention relates to isolated DNA segments which hybridize under stringent conditions to a DNA fragment having the nucleotide sequence set forth in SEQ ID NOs:1 or 53, preferably SEQ ID NO:1, or a unique fragment thereof and codes for a member of a mammalian DNA MSH5 gene. Stringent hybridization conditions are well known to the skilled artisan. For example, the hybridization conditions set forth in Example 1 can be used.

Identification and Classification of Tumors

One preferred assay described herein permits the diagnosis and/or prognosis of mismatch repair defective tumors. The eukaryotic nucleotide sequences, polypeptides, and antibodies of this invention are particularly useful for determining pathological conditions suspected of being tumors that: (i) contain a non-wild type allele of a MSH5 nucleotide sequence and/or (ii) lack at least one antigenic determinant on a polypeptide that is encoded by such nucleotide sequence and/or contain new antigenic determinants.

Using any technique known in the art including, for example, Southern blotting, Northern blotting, PCR, etc. (see, for example, Grompe, Nature Genetics 5:111-117, 1993, incorporated herein by reference) the nucleotide sequences of the present invention can be used to identify the presence of non-wild type alleles of sequences.

For example, in one embodiment, using SEQ ID NO.: 1 or 3-50, PCR primers can be designed to amplify individual exons or introns of human MSH5. These primers can then be used to identify and classify human tumors that contain at least one non-wild type allele of at least one sequence of the human gene corresponding to SEQ ID No.:1. Primer sets derived from SEQ ID NOS:3-50 can be used to amplify the individual exon of the human MSH5 gene. These primers all hybridize to intron sequences, and thus can be used to amplify exons and their flanking intron/exon junctions, including sequences important for splicing, from nucleic acid that has been isolated from a test sample, e.g., known tumor cells or cells suspected of being tumorous. The nucleotide sequences thus amplified can then be compared to the known, corresponding sequence to determine the presence or absence of any differences in the test sequences relative to wild type sequences. Tumors that contain at least one non-wild type allele of at least one sequence of the human gene can be classified as "mismatch repair defective". Comparisons of the sequences may be performed by direct sequence comparison or by other diagnostic methods known in the art including, but not limited to, single-strand conformational polymorphism analysis, denaturing polyacrylamide gel electrophoresis, and so on. (See, Grompe, supra.)

For instance, a primer set can be used to amplify sequences from a test tumor DNA and from control non-tumor DNA by standard PCR technique. For example, using PCR reactions that contained 10 mM Tris buffer pH 8.5, 50 mM KCL, 3 mM $MgCl_2$, 0.01 gelatin, 50 μM each dNTP, 1.5 unit Taq DNA polymerase, 5 pmole each primer, and 25 ng template DNA. 35 cycles of 30 sec at 94° C., 30 sec at 55° C., and 1 min at 72° C. can be performed. Product bands are then analyzed by the methods of Grompe supra. By such a method, differences can be observed in the sequences amplified between the test, e.g., tumor and non-tumor DNA. Alternatively, product bands can be sequenced using such oligonucleotides. Thus, even a single-base-pair difference can be observed between a test and control. Even changes located within intron sequences can affect pre-mRNA splicing signals.

Other primer pairs can be used that amplify only intron sequences or only exon sequences. Product bands can be analyzed as described above.

Alternatively, the antibodies of the invention can be used as probes in standard techniques such as Western blotting to detect the absence in tumor tissues of at least one antigenic determinant on at least one eukaryotic polypeptide encoded by nucleotide sequences that are homologous to MSH5 and/or the presence of new antigenic determinants. Test cells, e.g., cancers expressing abnormal proteins, would be expected to contain e.g. mismatch repair defective tumors, as described above.

The present invention can also indicate other factors in cells having an alteration. For example, the information provided by the isolated mammalian MSH5 sequences and isolated polypeptides of the invention can be used to inactivate, in a host cell, an endogenous MSH5 nucleotide sequence. Physiological characteristics of the resultant altered host cell can be analyzed and compared to physiological characteristics of an unaltered host cell. Any physiological characteristics of the altered host cell that are different from those of the unaltered host cell can be noted. The same physiological characteristics can then be analyzed in test cells such as tumor cells to help identify those tumors that contain a non-wild type allele.

Physiological characteristics that can be analyzed in such a study include, but are not limited to alterations in the rate of accumulation of spontaneous mutations (e.g. by the rate of spontaneous mutation to drug resistance), alterations in the rate of reversion of mutations, alterations in the frequency of recombination between divergent sequences, alterations in the genomic stability of short repeated sequences, sensitivity or resistance to agents that induce DNA damage such as UV-light, nucleotide analogs, alkylating agents, etc. For examples of protocols that may be used in this kind of analysis, see Reenan and Kolodner, Genetics 132: 975-985 (1992); Kat et al., Proc. Nat. Acad. Sci., USA, 90: 6424-6428 (1993); Strand et al., Nature, 365: 274-276 (1993), each of which is incorporated herein by reference.

We mapped MSH5 to chromosome 6 using PCR analysis. More specifically to 6p21.3 using PCR analysis. More specifically to 6p21.3 using PCR analysis of a radiation hybrid panel. Thus, one can look for polymorphisms in or near that region by known means. More preferably one looks at 6p21.3.

Classification of Nucleotide Sequences that are Homologous to a Bacterial Mismatch Repair Gene Different versions, or "alleles" of the mammalian MSH5 nucleotide sequences of the invention can be classified by their ability to functionally replace an endogenous nucleotide sequence, in a normal host cell. As used herein, a "wild type" allele is defined as a sequence that can replace an endogenous nucleotide sequence in a normal host cell without having detectable adverse effects on the host cell. A "non-wild type" allele or "alteration" is defined as a mammalian MSH5 nucleotide sequence that cannot replace an endogenous nucleotide sequence in a normal host cell without having detectable adverse effects on the host cell.

Non-wild type alleles of MSH5 nucleotide sequence of the invention can differ from wild type alleles in any of several ways including, but not limited to, the amino acid sequence of an encoded polypeptide and the level of expression of an encoded nucleotide transcript or polypeptide product.

Physiological properties that can be monitored include, but are not limited to, growth rate, rate of spontaneous mutation to drug resistance, rate of gene conversion, genomic stability of short repeated DNA sequences, sensitivity or resistance to DNA damage-inducing agents such as UV light, nucleotide analogs, alkylating agents and so on. For example, defective MSH5 genes confer resistance to alkylating agents.

Particular "non-wild type" alleles that encode a protein that, when introduced into a host cell, interferes with the endogenous gene, are termed "dominant negative" alleles.

Inactivation in a Host Cell of Endogenous Nucleotide Sequences

The information provided by the isolated nucleotide sequences and isolated polypeptides of the invention can be used to inactivate, for example, an endogenous nucleotide sequence that is homologous to a MSH5 gene and/or a polypeptide product encoded by an endogenous nucleotide sequence that is homologous to such gene in a host cell.

For example, non-wild type alleles of MSH5, can be used to inactivate endogenous nucleotide sequences in a host cell by, for example, hybridizing to the endogenous nucleotide sequences and thereby preventing their transcription or translation, or by integrating into the genome of the host cell and thereby replacing or disrupting an endogenous nucleotide sequence. More specifically, a non-wild type allele that can bind to an endogenous DNA sequences, for example to form a triple helix, could prevent transcription of endogenous sequences. A non-wild type allele that, upon transcription, produces an "antisense" nucleic acid sequence that can hybridize to a transcript of an endogenous sequence could prevent translation of the endogenous transcript. A non-wild type allele, particularly one containing an insertion or deletion of nucleotide sequences, could integrate into the host cell genome and thereby replace or disrupt an endogenous sequence.

In one embodiment, the amount of polypeptide expressed by an endogenous MSH5 gene may be reduced by providing polypeptide-expressing cells, preferably in a transgenic animal, with an amount of MSH5 gene anti-sense RNA or DNA effective to reduce expression of mismatch repair gene polypeptide.

A transgenic animal (preferably a non-human mammal) could alternatively be provided with a repressor protein that can bind to a specific DNA sequence, thereby reducing ("repressing") the level of transcription of MSH5 gene.

Transgenic animals of the invention which have attenuated levels of polypeptide expressed by MSH5 gene(s) have general applicability to the field of transgenic animal generation, as they permit control of the level of expression of genes.

Mutagenesis of Eukaryotic Nucleotide Sequences that are Homologous to a Bacterial Mismatch Repair Gene The isolated nucleotide sequences and isolated polypeptides of the invention can be mutagenized by any of several standard methods including treatment with hydroxylamine, passage through mutagenic bacterial strains, etc. The mutagenized sequences can then be classified "wild type" or "non-wild type" as described above.

Mutagenized sequences can contain point mutations, deletions, substitutions, rearrangements etc. Mutagenized sequences can be used to define the cellular function of different regions of the polypeptides they encode. For example, the portion involved in chromosomal segregation can be mutagenized to delete such portion to confirm function.

Diagnosis of Susceptibility to an MSH5 Related Defect Such as Cancer or Inappropriate Chromosomal Segregation The MSH5 nucleotide sequences, polypeptides, and antibodies of this invention are particularly useful for diagnosis e.g. of susceptibility to cancers whose incidence correlates with an alteration of a member of the pathway, as described. Such cancers would be expected to contain mismatch repair defective tumors, as described above.

Using any technique known in the art, such as Southern blotting, Northern blotting, PCR, etc. (see, for example, Grompe, supra) the nucleotide sequences of the present invention can be used to identify the presence of relevant non-wild type alleles of MSH5.

Alternatively, the antibodies of the invention can be used as probes in standard techniques such as Western blotting to detect the absence of at least one relevant antigenic determinant on at least one polypeptide encoded by MSH5 nucleotide sequences in sample tissues from individuals being tested for susceptibility to a condition associated with an MSH5 defect such as a chromosomal segregation difficulty or cancer.

In preferred embodiments one would also test for defects in other mismatch repair genes such as MSH2, MLH1, MSH3, MSH6, etc.

Identification of Effective Therapeutic Agents

Molecules and host cells provided by the invention can be used to identify therapeutic agents effective against MSH5 defects. In particular, the molecules and host cells of the invention could be used to identify therapeutic agents effective against MSH5 defects such as cancers. For example, the presence of a non-wild type allele of MSH5 and/or with the lack of at least one antigenic determinant on a polypeptide that is encoded by such a nucleotide sequence.

For instance, as described above, altered host cells can be generated in which an endogenous MSH5 nucleotide sequence has been inactivated and/or in which a MSH5 polypeptide product has been inactivated. Such an altered host cell can be contacted with various potential therapeutic agents or combinations thereof. Physiological effects of such therapeutic agents or combinations thereof can be assayed by comparing physiological characteristics of an altered host cell that has been contacted with the therapeutic agents or combinations thereof to the physiological characteristics of an unaltered host cell that has been contacted with the therapeutic agents or combinations thereof.

In preferred embodiments, the altered host cell is a mammalian cell, for example, a human cell, either in tissue culture or in situ (preferably non-human). Other eukaryotic cells such as yeast, may also be used. Potential therapeutic reagents that may be tested include, but are not limited to, intercalating agents, nucleotide analogs, and X-rays. Possible physiological effects that may be assayed include, but are not limited to, alterations in the rate of accumulation of spontaneous mutations (e.g. by the rate of spontaneous mutation to drug resistance), alterations in chromosomal segregation during meiosis, alterations in meiotic crossing over, alterations in the rate of reversion of mutations, alterations in the frequency of recombination between divergent sequences, alterations in the genomic stability of short repeated sequences, sensitivity or resistance to agents that induce DNA damage such as UV-light, nucleotide analogs, alkylating agents, and so on. Preferred therapeutic agents or combinations thereof can be selected.

Preferred cancer therapeutic agents include therapeutic agents or combinations thereof that are relatively toxic to the altered cell as compared to the unaltered cell. Toxicity can be defined in terms of parameters such as increased cell death (assayed by cell count), decreased DNA replication (assayed by, for example, incorporation of titrated thymidine ($^3$H), and slowed cell growth rate (assayed by cell count).

In one particular embodiment of the invention, altered and unaltered host cells can be contacted with therapeutic agents or combinations thereof in the presence of DNA damaging agents, for example nucleotide analogs (e.g. 5-FU, 2AP), UV Light, or alkylating agents. It might be expected that DNA damaging agents alone would be lethal to altered host cells containing an endogenous, but inactivated nucleotide sequence or polypeptide product of the invention because the nucleotide analogs would be incorporated into the DNA, creating mutations that cannot be repaired in the absence of a functional mismatch repair system. However, such an effect has not been observed in analogous systems. Nonetheless, it is likely that DNA-damaging agents, when combined with other therapeutic agents, would be relatively toxic to altered cells.

The assays described herein allow for the identification of therapeutic cancer agents or combinations thereof that, when administered in the presence of DNA damaging or other agents, would be relatively toxic to an altered host cell containing an inactivated endogenous nucleotide sequence of the invention and/or an inactivated polypeptide product of the invention as compared to an unaltered cell.

Alternative preferred therapeutic agents include those that, when administered, restore the physiological characteristics of the altered cell that has been contacted with the therapeutic reagents, or combination thereof, to more closely resemble the physiological characteristics of an unaltered, untreated host cell. It is further preferred that these therapeutic agents, or combinations thereof, do not significantly affect the physiological characteristics of an unaltered host cell.

Therapeutic and Pharmaceutic Compositions

The nucleotide sequences and polypeptides expressed by these sequences described herein can also be used in pharmaceutical compositions in, for example, gene therapy. An exemplary pharmaceutical composition is a therapeutically effective amount of a MSH5 sequence of the invention optionally included in a pharmaceutically-acceptable and compatible carrier. The term "pharmaceutically-acceptable and compatible carrier" as used herein, and described more fully below, refers to (i) one or more compatible solid or liquid filler diluents or encapsulating substances that are suitable for administration to a human or other animal, and/or (ii) a system, such as a retroviral vector, capable of delivering the MSH5 nucleotide sequence to a target cell. In the present invention, the term "carrier" thus denotes an organic or inorganic ingredient, natural or synthetic, with which the mismatch repair nucleotide sequences and polypeptides of the invention are combined to facilitate application. The term "therapeutically-effective amount" is that amount of the present pharmaceutical compositions which produces a desired result or exerts a desired influence on the particular condition being treated. Various concentrations may be used in preparing compositions incorporating the same ingredient to provide for variations in the age of the patient to be treated, the severity of the condition, the duration of the treatment and the mode of administration.

The term "compatible", as used herein, means that the components of the pharmaceutical compositions are capable of being commingled with the nucleic acid and/or polypeptides of the present invention, and with each other, in a manner such that there is no interaction that would substantially impair the desired pharmaceutical efficacy.

Dose of the pharmaceutical compositions of the invention will vary depending on the subject and upon particular route of administration used. By way of an example only, an overall dose range of from about, for example, 1 microgram to about 300 micrograms is contemplated for human use. This dose can be delivered on at least two separate occasions, preferably spaced apart by about 4 weeks. Pharmaceutical compositions of the present invention can also be administered to a subject according to a variety of other, well-characterized protocols. For example, certain currently accepted immunization regimens can include the following: (i) Recommended administration times are a first dose at elected date; a second dose at 1 month after first dose; and a third dose at 5 months after second dose. See Product Information, Physician's Desk Reference, Merck Sharp & Dohme (1990), at 1442-43. (e.g., Hepatitis B Vaccine-type protocol); (ii) Recommended administration for children is first dose at elected date (at age 6 weeks old or older); a second dose at 4-8 weeks after first dose; a third dose at 4-8 weeks after second dose; a fourth dose at 6-12 months after third dose; a fifth dose at age 4-6 years old; and additional boosters every 10 years after last dose. See Product Information, Physician's Desk Reference, Merck Sharp & Dohme (1990), at 879 (e.g., Diptheria, Tetanus and Pertussis-type vaccine protocols). Desired time intervals for delivery of multiple doses of a particular composition can be determined by one of ordinary skill in the art employing no more than routine experimentation.

The polypeptides of the invention may also be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulfuric, nitric, phosphoric, maleic, acetic, salicylic, p-toluene-sulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acid and/or polypeptides of the invention together with one or more pharmaceutically acceptable carriers thereof and optionally any other therapeutic ingredients.

The compositions include those suitable for oral, rectal, topical, nasal, ophthalmic or parenteral administration, all of which may be used as routes of administration using the materials of the present invention. Other suitable routes of administration include intrathecal administration directly into spinal fluid (CSF), direct injection onto an arterial surface and intraparenchymal injection directly into targeted areas of an organ. Compositions suitable for parenteral administration are preferred. The term "parenteral" includes subcutaneous injections, intravenous, intramuscular, intrasternal injection or infusion techniques.

The compositions may conveniently be presented in unit dosage form and may be prepared by any of the methods well known in the art of pharmacy. All methods include the step of bringing the active ingredients of the invention into association with a carrier which constitutes one or more accessory ingredients.

Compositions of the present invention suitable for oral administration may be presented as discrete units such as capsules, cachets, tablets or lozenges, each containing a predetermined amount of the nucleic acid and/or polypeptide of the invention in liposomes or as a suspension in an aqueous liquor or non-aqueous liquid such as a syrup, an elixir, or an emulsion.

Preferred compositions suitable for parenteral administration conveniently comprise a sterile aqueous preparation of the nucleic acid and/or polypeptides of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The nucleic acids and/or polypeptides of the present invention can also be conjugated to a moiety for use in vaccines. The moiety to which the nucleic acids and/or polypeptides is conjugated can be a protein, carbohydrate, lipid, and the like. The chemical structure of this moiety is not intended to limit the scope of the invention in any way. The moiety to which nucleic acids and/or polypeptides may be bound can also be an adjuvant. The term "adjuvant" is intended to include any substance which is incorporated into or administered simultaneously with the nucleic acids and/or polypeptides of the invention which potentiates the immune response in the subject. Adjuvants include aluminum compounds, e.g., gels, aluminum hydroxide and aluminum phosphate gels, and Freund's complete or incomplete adjuvant. The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U), leutinan, pertussis toxin, lipid A, saponins and peptides, e.g., murarnyl dipeptide. Rare earth salts, e.g., of lanthanum and cerium, may also be used as adjuvants. The amount of adjuvant required depends upon the subject and the particular therapeutic used and can be readily determined by one skilled in the art without undue experimentation.

Identification of Factors that Interact with MSH5 Polypeptide Products of the Invention The nucleotide sequences and polypeptides of the invention can be used to identify interacting factors. Identifying those proteins that interact with the polypeptide of SEQ ID NO.:2 should further identify other proteins that act in mismatch repair. Yeast provides a particularly powerful system for genetic identification of interacting factors. In addition to genetic methods, several biochemical methods, such as co-immunoprecipitation and protein affinity chromatography can be used to identify interacting proteins.

Biochemical Methods

In one embodiment of the invention, co-immunoprecipitation is used to identify proteins that interact with the isolated polypeptides of the invention, such as the polypeptides of SEQ ID NOS.:2 and SEQ ID NO.:54. Co-immunoprecipitation has proven useful for identifying interacting proteins (see, for example, Kolodziej and Young, Methods Enzymol. 194:508, 1991, incorporated herein by reference; Pallas et al., J. Virol 62:3934, 1988, incorporated herein by reference).

In one preferred embodiment of the invention, the polypeptide of SEQ ID NO.:2 may be engineered using standard methods to contain a flu 12CA5 epitope tag (Kolodziej and Young, supra) at either or both the N-terminus and the C-terminus. It may be necessary to insert the epitope at internal locations. The tagged protein may then tested for the ability to provide mismatch repair function in yeast cells whose endogenous copy of the MSH5 gene has been inactivated. If functional tagged proteins cannot be produced, polyclonal or monoclonal antisera raised against antigenic determinants on the polypeptide of SEQ ID NO.:2 may be used.

Tagged protein is expressed in log or stationary phase, in mitotic cells or in meiotic cells. Different levels of expression (e.g. native promoter, cen vector; GAL10 promoter, cen vector; GAL10 promoter, 2 F based vector) can be tested. The cells are lysed and the tagged protein is precipitated using the flu 12CA5 antibody (or the polyclonal antisera raised against SEQ ID NO.:2 determinants) and analyzed by one and two dimensional gel electrophoresis to detect proteins that co-precipitate (Koloddziej and Young 1991, supra; Pallas et al., supra).

The specificity of co-precipitation is evaluated in experiments in which untagged, rather than tagged protein is expressed and in which tagged protein is expressed and control mouse antisera are substituted for the flu 12CA5 antibody. Sensitivity to salt and different detergents like SDS, NP40 and digitonin are used to evaluate the stability and specificity of observed interactions. The possibility that such interactions require mispaired bases can be tested by adding oligonucleotide duplexes containing mispaired bases and control oligonucleotide duplexes lacking mispaired bases to the cell extracts prior to addition of antibody.

If interacting proteins are found, gel electrophoresis or immunaffinity chromatography can be used to purify sufficient amounts to obtain N-terminal and internal protein sequences by standard techniques (see, for example, Matsudaira J. Biol. Chem. 262:10035-10038, 1987, incorporated herein by reference). This sequence information can then be used for comparison with DNA and protein databases and for cloning the genes encoding the proteins for use in reverse genetics analysis and protein overproduction. An identical protocol may be performed with the polypeptide of SEQ ID NO.: 54, or any other polypeptide that is encoded by a MSH5 nucleotide sequence of the invention.

In another embodiment of the invention, proteins that interact with the polypeptides of the invention, in particular with polypeptides of SEQ ID NOS.:2 and/or 54, may be identified using a protein affinity column on which these proteins are immobilized. (See, Formosa et al., Proc. Nat. Acad. Sci., USA, 80:2442, 1983. For example, 1 to 10 mg of protein can be covalently linked to AffiGel-10 (made by BioRad Laboratories, Richmond, Calif.) or equivalent matrix. Parallel chromatography experiments on a column containing a polypeptide of the invention (e.g., SEQ ID NO.: 2) and a control BSA column can be performed to identify proteins that specifically bind to the polypeptide of the invention. Identified interacting proteins can be N-terminal sequenced as described above. Also, antibodies can be produced to react with identified interacting proteins. Such antibodies can then be used, for example, to screen expression libraries to facilitate cloning of genes that encode the identified interacting proteins. Once interacting proteins have been identified and isolated, biochemical experiments may be performed to assess the functional significance of their interaction with the polypeptides of the invention (e.g., SEQ ID NO.:2). Such experiments include determining: 1) if the interacting protein(s) enhance a specific activity such as the mispair binding activity of the polypeptide of the invention; 2) if the interacting protein(s) restore function to inactive in vitro systems; and 3) if the interacting protein(s) substitute for any required protein fractions in in vitro reconstitution experiments. For a description of a representative in vitro system, see Muster-Nassal and Kolodner, Proc. Nat. Acad. Sci., USA,83:7618 (1986), incorporated herein by reference.

Biochemical methods can also be used to test for specific interactions between isolated polypeptides of the invention and already known proteins, for example proteins involved in DNA replication or recombination. In one approach, these known proteins can be immobilized on nitrocellulose filters or other supports, the support blocked to prevent non-specific binding, incubated with an epitope-tagged polypeptide of the invention and then probed with antibody reactive with the epitope tag (for example, the 12CA5 flu antibody) to detect epitope-tagged polypeptides of the invention that have bound to the filter by interaction with the immobilized known protein. Non-epitope-tagged polypeptides of the invention can be used instead in combination with antisera reactive against antigenic determinants of those polypeptides.

When interacting proteins have been cloned, standard methods including mutagenesis and others described in this application can be used to determine the cellular function(s) of those proteins, e.g., mismatch repair, chromosomal segregation, other types of DNA repair, DNA replication, recombination, and so on.

Once proteins have been identified that interact with an isolated polypeptide of the invention, similar types of experiments can be performed to identify proteins that interact with those newly identified proteins. By systematically applying this approach, it may be possible to identify a number of proteins that function in mismatch repair and simultaneously gain insight into the mechanism by which they act.

Genetic Methods

Alternately, or additionally, genetic methods can also be used to identify proteins that interact with polypeptides of the invention.

For example, one method is the two hybrid system described by Chien et al., Proc. Nat. Acad. Sci. USA., 88:9578 (1991), incorporated herein by reference. This method may be used to identify proteins that interact with polypeptides of the invention. For example, the N-terminal half of SEQ ID NO.:2 may contain at least one region that interacts with other proteins (Reenan and Kolodner, Genetics 132:963, supra). This region may be fused at the end of amino acids 1-147 of the Gal4 protein to make a fusion protein that will bind to the Gal4 site in DNA.

The fusion protein can then be used to screen an available library of yeast DNA fragments fused to the Gal4 activation domain for activation of a GAL1-LacZ reporter. Positives can be rescreened to eliminate plasmids from the library that activate in the absence of the SEQ ID NO.:2 polypeptide segment. The remaining positive clones may be used to isolate disruptions of the yeast genes from which the sequences on the library plasmids originated. Cells containing such disruptions may be analyzed to determine if the disruptions affect spontaneous mutation rate, gene conversion, repair of plasmids containing mispaired bases, and/or genomic stability of short repeated DNA sequences, as would be expected for disruption of a gene involved in mismatch repair. This method is rapid since the required libraries are readily available from any of several sources, for example, Dr. Roger Brent at the Massachusetts General Hospital. It is straightforward to determine if any cloned genes have properties consistent with a role in mismatch repair. Libraries of DNA fragments from eukaryotic organisms other than yeast that are fused to Gal4 for an activation domain can also be screened. Such libraries can be made by using standard methods.

An alternate genetic method that can be used to identify proteins that interact with polypeptides of the invention and the genes that encode them is to use secondary mutation analysis. For example, yeast cells or mammalian cells carrying a mutation in the MSH5 gene, corresponding to SEQ ID NO.:1 or other mammalian homologue can be mutagenized and screened to identify secondary mutations that either correct or augment the mismatch repair defects of the original, MSH5 disrupted cells. Mutagenized cells can be assayed for effects on, for example, spontaneous mutation rate, gene conversion, repair of plasmids containing mispaired bases, and genomic stability of short repeated DNA sequences, as already described in this application.

Secondary mutations that correct defects of the MSH5-disrupted cells are termed "suppressors". Suppressor mutations can be isolated in genes that interact with MSH5. For explanation of the logic in isolating suppressor mutations and protocols involved see, for example, Adams and Botstein, Genetics 121: 675-683 (1989); Novick et al., Genetics 121: 659-674 (1989); Jarvik and Botstein, Proc. Nat. Acad. Sci. USA 72: 2738-2742 (1975), all of which are incorporated herein by reference. Those genes can then be cloned and sequenced by standard protocols.

Secondary mutations that augment the mismatch repair defects of the original, MSH5-disrupted cells can sometimes have extreme effects, to the extent the mutagenized cells are no longer viable. Such secondary mutations are referred to as "synthetic lethals". For an explanation of the logic and protocols involved in identifying these mutations, see Kranz and Holm, Proc. nat. Acad. Sci., USA 87: 6629-6633, (1990), incorporated herein by reference. The effects of synthetic lethal mutations can be assayed in the presence or absence of DNA damaging agents such as UV light, nucleotide analogs, alkylating agents, etc. As mentioned above, it is desirable for the possible development of therapeutic agents effective against cancer to identify circumstances under which DNA damaging agents are lethal to host cells bearing an inactivated eukaryotic nucleotide sequence of the invention. In this case, studies of synthetic lethality in yeast can be used to identify genes that, when mutated, render MSH5-disrupted cells sensitive to DNA damaging agents.

Such genes would be logical targets for chemotherapy development. Agents, such as antisense reagents or other soluble enzyme inhibitors, for example, that inactivate such genes might render tumors having an altered endogenous copy of SEQ ID NO.:1; sensitive to DNA damaging agents such as nucleotide analogs, light, alkylating agents, or other therapeutic agents.

Expression of Pathway Members

Recombinant vectors containing nucleotide sequences of the invention can be introduced into host cells by, for example, by transformation, transfection, infection, electroporation, etc. Recombinant vectors can be engineered such that the mammalian nucleotide sequences of the invention are placed under the control of regulatory elements (e.g. promoter sequences, polyadenylation signals, etc.) in the vector sequences. Such regulatory elements can function in a host cell to direct the expression and/or processing of nucleotide transcripts and/or polypeptide sequences encoded by the mammalian nucleotide sequences of the invention.

Expression systems can utilize prokaryotic and/or eukaryotic (i.e., yeast, human) cells. See, for example, "Gene Expression Technology", Volume 185, *Methods in Enzymology*, (ed. D. V. Goeddel), Academic Press Inc., (1990) incorporated herein by reference. A large number of vectors have been constructed that contain powerful promoters that generate large amounts of mRNA complementary to cloned sequences of DNA introduced into the vector. For example, and not by way of limitation, expression of eukaryotic nucleotide sequences in *E. coli* may be accomplished using lac, trp, lambda, and recA promoters. See, for example, "Expression in *Escherichia coli*", Section II, pp. 11-195, V. 185, *Methods in Enzymology*, supra; see also Hawley, D. K., and McClure, W. R., "Compilation and Analysis of *Escherichia coli* promoter DNA sequences", Nucl. Acids Res., 11: 4891-4906 (1983), incorporated herein by reference. Expression of mammalian nucleotide sequences of the invention, and the polypeptides they encode, in a recombinant bacterial expression system can be readily accomplished.

Yeast cells suitable for expression of the mammalian nucleotide sequences of the invention, and the polypeptides they encode, include the many strains of *Saccharomyces cerevisiae* (see above) as well as *Pichia pastoris*. See, "Heterologous Gene Expression in Yeast", Section IV, pp. 231-482, V. 185, *Methods in Enzymology*, supra, incorporated herein by reference. Moreover, a large number of vector-mammalian host systems known in the art may be used. See, Sambrook et al., Volume III, supra and "Expression of Heterologous Genes in Mammalian Cells", Section V, pp. 485-596, V. 185, *Methods in Enzymology*, supra, incorporated herein by reference.

Suitable expression systems include those that transiently or stably expressed DNA and those that involve viral expression vectors derived from simian virus 40 (SV 40), retroviruses, and baculoviruses. These vectors usually supply a promoter and other elements such as enhancers, splice acceptor and/or donor sequences, and polyadenylation signals. Possible vectors include, but are not limited to, cosmids, plasmids or modified viruses, but the vector system must be compatible with the host cell used. Viral vectors include, but are not limited to, vaccinia virus, or lambda derivatives. Plasmids include, but are not limited to, pBR322, pUC, or Bluescript7 (Stratagene) plasmid derivatives. Recombinant molecules can be introduced into host cells via transformation, transfection, infection, electroporation, etc. Generally, expression of a protein in a host is accomplished using a vector containing DNA encoding that protein under the control of regulatory regions that function in the host cell.

In particular, expression systems that provide for overproduction of a MSH5 protein can be prepared using, for example, the methods described in U.S. Pat. No. 4,820,642 (Edman et al., Apr. 11, 1989), incorporated herein by reference. The general requirements for preparing one form of expression vector capable of overexpression are: (1) the presence of a gene (e.g., a prokaryotic gene) into which a MSH5 nucleotide sequence can be inserted; (2) the promoter of this prokaryotic gene; and (3) a second promoter located upstream from the prokaryotic gene promoter which overrides the prokaryotic gene promoter, resulting in overproduction of the extracellular matrix protein. The second promoter is obtained in any suitable manner. Possible host cells into which recombinant vectors containing eukaryotic nucleotide sequences of the invention can be introduced include, for example, bacterial cells, yeast cells, mammalian cells in tissue culture or in situ.

Eukaryotic nucleotide sequences of the invention that have been introduced into host cells can exist as extra-chromosomal sequences or can be integrated into the genome of the host cell by homologous recombination, viral integration, or other means.

Standard techniques such as Northern blots and Western blots can be used to determine that introduced sequences are in fact being expressed in the host cells.

The MSH5 gene can be introduced into a host (target) cell by any method which will result in the uptake and expression of the MSH5 gene by the target cells. These can include vectors, liposomes, naked DNA, adjuvant-assisted DNA, catheters, etc. Vectors include chemical conjugates such as described in WO 93/04701, which has a targeting moiety (e.g. a ligand to a cellular surface receptor) and a nucleic acid binding moiety (e.g. polylysine), viral vectors (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., *J. Neurochem*, 64:487 (1995); Lim, F., et al., in DNA Cloning: *Mammalian Systems*, D. Glover, Ed. (Oxford Univ. Press, Oxford England) (1995); Geller, A. I. et al., *Proc Natl. Acad. Sci.*: U.S.A.:90 7603 (1993); Geller, A. I., et al., *Proc Natl. Acad. Sci USA:* 87:1149 (1990)], adenovirus vectors [LeGal LaSalle et al., *Science*, 259:988 (1993); Davidson, et al., *Nat. Genet* 3: 219 (1993); Yang, et al., *J. Virol.* 69: 2004 (1995)] and adeno-associated virus vectors [Kaplitt, M. G., et al. *Nat. Genet.* 8:148 (1994)].

Pox viral vectors introduce the gene into the cells cytoplasm. Avipox virus vectors result in only a short term expression of the MSH5 gene. Adenovirus vectors, adeno-associated virus vectors and herpes simplex virus (HSV) vectors are preferred for introducing the MSH5 gene into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include naked DNA, CaPO$_4$ precipitation, DEAE dextran, electroporation, protoplast fusion, lipofection, cell microinjection, viral vectors, etc.

In one method of expressing a human MSH5 nucleotide sequence and the polypeptide it encodes, a cDNA clone that contains the entire coding region of the polypeptide (e.g. SEQ ID NO.:1) is cloned into a eukaryotic expression vector and transfected into cells such as cells derived from the simian kidney (e.g., COS-7 cells). Expression is monitored after transfection by, for example, Northern, Southern, or Western blotting.

Host cells carrying such introduced sequences can be analyzed to determine the effects that sequence introduction has on the host cells. In particular, cells could be assayed for alterations in the rate of accumulation of spontaneous mutations (e.g. by the rate of spontaneous mutation to drug resistance), in the rate of reversion of mutations, in the frequency of homologous recombination, in the frequency of recombination between divergent sequences, or in the genomic stability of short repeated sequences. In particular, mammalian cells carrying introduced sequences of the invention could be tested for the stability of di- and trinucleotide repeats by the method of Schalling et al. (Schalling et al. Nature. Genetics, 4:135, 1993, incorporated herein by reference.), or for sensitivity to agents that induce DNA damage such as UV-light, nucleotide analogs, etc.

In particular embodiments, a nucleotide sequence of the invention may be used to inactivate an endogenous gene by homologous recombinations, and thereby create a MSH5 gene-deficient cell, tissue, or animal. For example, and not by way of limitation, a recombinant human nucleotide sequence of the present invention may be engineered to contain an insertional mutation (e.g., the neo gene) which, when inserted, inactivates transcription of an endogenous MSH5 gene. Such a construct, under the control of a suitable promoter operatively linked to a nucleotide sequence of the invention, may be introduced into a cell by a technique such as transformation, transfection, transduction, injection, etc. In particular, stem cells lacking an intact endogenous MSH5 gene may generate transgenic animals deficient in that mismatch repair gene, and the polypeptide it encodes, via germ line transmission.

In a specific embodiment of the invention, an endogenous MSH5 gene in a cell may be inactivated by homologous recombination with a mutant MSH5 gene, thereby allowing the development of a transgenic animal from that cell, which animal lacks the ability to express the encoded mismatch repair gene polypeptide. In another embodiment, a construct can be provided that, upon transcription, produces an Aantisense" nucleic acid sequence which, upon translation, will not produce the required mismatch repair gene polypeptide.

A Atransgenic animal@ is an animal having cells that contain mammalian DNA which has been artificially inserted into a cell, which DNA becomes part of the genome of the animal that develops from that cell. The preferred DNA contains human MSH5 nucleotide sequences. The mammalian gene may be entirely foreign to the transgenic animal or may be identical to the natural gene of the animal, but which is inserted into the animal's genome at a location which differs from that of the natural copy. Transgenic animals provide good model systems for studying the development of cancer, problems with chromosomal segregation the effects of potential therapeutic reagents, and the carcinogenicity of chemical agents administered to the animals.

Functional Equivalents and Unique Fragments of Isolated Nucleotide Sequences and Polypeptides This invention pertains to isolated mammalian MSH5 nucleotide sequences their functional equivalents, or unique fragments of these sequences, that may be used in accordance with this the invention. Nucleotide sequences or "probes" that are capable of hybridizing are also included. Additionally, the isolated polypeptides encoded by these sequences, and unique fragments of the polypeptides, may also be used in accordance with the invention. The polypeptides can be used, for example to raise an antibody to a unique sequence.

The term "unique fragment" refers to any portion of a mammalian MSH5 nucleotide sequence or polypeptide of the invention that as of the filing date of this application has been found only among the nucleotide or amino acid sequences and has not otherwise been identified as of this date in a public data base.

For example, because the exact nucleotide MSH5 sequence is known for two mammalian homologues (SEQ ID NOs.:1 and 54) one of ordinary skill in the art can readily determine the portions of the human or murine homologues that have not been publicly found in other nucleotide sequences as of the filing date. Moreover, numerous public data bases are known and one can rapidly compare a putative unique sequence with the database.

The term "unique fragment" can refer to a nucleotide or amino acid sequences that is found in all mammalian MSH5 homologues or their encoded proteins, or to nucleotide or amino acid sequences that are found in only one homologue (e.g., human) and absent from other homologues (e.g., murine).

"Unique fragments" can be practically defined by the use of computer programs capable of comparing nucleic acid and/or polypeptide sequences. In particular a computer program such as the HYPERBLAST program (Altschul et al. J. Mol. Biol. 215:403-410, 1990, incorporated herein by reference) can be used to translate a DNA sequence in all possible reading frames and then to search known databases (e.g. GenBank, PIR, SWIS-PROT) for similar or identical sequences.

PCR can be used to generate unique fragments of the homologues of the invention.

Preferred unique fragments of a nucleotide sequence are between length 15 and 6000 nucleotides (nt.), with particularly preferred fragments being less than approximately 3000 nt long. Preferably, the fragment is at least 6 amino acids, more preferably at least 20 nucleotides in length. More preferably, the fragment is at least 25 nucleotides. Unique fragments of a nucleotide sequence may be single-stranded.

Preferred unique fragments of a polypeptide are between approximate 5 and 100 amino acids in length. More preferably at least 12 amino acids in length, still more preferably at least 20 amino acids in length.

The term "functional equivalent", when applied to the nucleotide sequences of the invention, describes a sequence that satisfies one of the following conditions: (i) the nucleotide sequence in question can hybridize to a MSH5 nucleotide sequence, but it does not necessarily hybridize to that sequence with an affinity that is the same as that of the naturally occurring nucleotide sequence (ii) the nucleotide sequence in question can serve as a probe to distinguish between MSH5 nucleotide sequences and other nucleotide sequences.

For example, the human cDNA clone SEQ ID NO.:1 is an MSH5 gene. However, due to normal sequence variation within the human population, clones derived from different libraries would likely show sequence variability relative to the clone of SEQ ID NO.:1. In particular, in some instances, the phenomenon of codon degeneracy (see below), will contribute to nucleotide differences without differences in the amino acid sequence of the encoded protein. In other cases, even the protein sequence may vary somewhat. In most instances, the changes are insignificant and the nucleotide and amino acid sequences are functionally equivalent. As discussed below, such equivalence can be empirically determined by comparisons of structural and/or functional characteristics.

Due to the degeneracy of nucleotide coding sequences (see Alberts et al., Molecular Biology of the Cell, Garland Publishing, New York and London, 1989- page 103, incorporated herein by reference), other nucleic acid sequences may be used in the practice of the present invention. These include, but are not limited to, sequences based upon SEQ ID NO:1 that have been altered by the substitution of different codons encoding the same amino acid residue within the sequence, thus producing a silent change. Almost every amino acid except tryptophan and methionine is represented by several codons. Often the base in the third position of a codon is not significant, because those amino acids having 4 different codons differ only in the third base. This feature, together with a tendency for similar amino acids to be represented by related codons, increases the probability that a single, random base change will result in no amino acid substitution or in one involving an amino acid of similar character. Such degenerate nucleotide sequences are regarded as functional equivalents of the specifically claimed sequences.

The nucleotide sequences of the invention (e.g. SEQ ID NOs.:1-54) can be altered by mutations such as substitutions, additions or deletions that provide for functionally equivalent nucleic acid sequence. In particular, a given nucleotide sequence can be mutated in vitro or in vivo, to create variations in coding regions and/or to form new restriction endonuclease sites or destroy preexisting ones and thereby to facilitate further in vitro modification. Any technique for mutagenesis known in the art can be used including, but not limited to, in vitro site-directed mutagenesis (Hutchinson, et al., J. Biol. Chem. 253:6551, 1978), use of TAB7 linkers (Pharmacia), PCR-directed mutagenesis, and the like. The functional equivalence of such mutagenized sequences, as compared with un-mutagenized sequences, can be empirically determined by comparisons of structural and/or functional characteristics.

According to the invention, an amino acid sequence is Afunctionally equivalent" compared with the sequences depicted in, for example, SEQ ID NO.:2 if the amino acid sequence contains one or more amino acid residues within the sequence which can be substituted by another amino acid of a similar polarity which acts as a functional equivalent. The term "functionally equivalent", when applied to the amino acid sequences of the invention, also describes the relationship between different amino acid sequences whose physical or functional characteristics are substantially the same. Substitutions, deletions or insertions of amino acids often do not produce radical changes in the physical and chemical characteristics of a polypeptide, in which case polypeptides containing the substitution, deletion, or insertion would be considered to be functionally equivalent to polypeptides lacking the substitution, deletion, or insertion.

Functionally equivalent substitutes for an amino acid within the sequence may be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Substantial changes in functional or, for example, immunological properties may be avoided by selecting substitutes that do not differ from the original amino acid residue. More significantly, the substitutions can be chosen for their effect on: (i) maintaining the structure of the peptide backbone in the area of the substitution, for example, as a sheet or helical conformation; (ii) maintaining the charge or hydrophobicity of the molecule at the target side; or (iii) maintaining the bulk of the side chain. The substitutions that in general could expected to induce greater changes, and therefore should be avoided, are those in which: (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl, or (e) a residue having a bulky side chain, e.g., phenylalanine, is substituted for one (or by) one not having such a side chain, e.g., glycine.

Most deletions and insertions in a MSH5 polypeptide and substitutions in particular, are not expected to produce radical changes in the characteristics of the polypeptide. Nevertheless, when it is difficult to predict the exact effect of the substitution, deletion, or insertion in advance of doing so, one skilled in the art will appreciate that the effect will be evaluated using routine screening assays as described herein and known in the art. For example, a change in the immunological character of a human MSH5 gene product, such as binding to a given antibody, can be measured by an immunoassay such as a competitive type immunoassay.

The functional equivalence of two polypeptide sequences can be assessed by examining physical characteristics (e.g. homology to a reference sequence, the presence of unique amino and sequences, etc.) and/or functional characteristics analyzed in vitro or in vivo. For example, looking at functional equivalents of the proteins of SEQ ID NO.:2. These functional equivalents may also contain a helix-turn-helix DNA binding motif, a $Mg^{2+}ATP$ binding domain, and/or the amino acid sequence TGPNM. These functional equivalents may also be capable of binding to mismatched base pairs in, for example, a filter-binding assay.

Functional equivalents may also produce a dominant MSH5 defective phenotype when expressed in *E. coli*, as detected in an assay described herein, or may otherwise behave like MSH5 proteins in other assays herein described or known in the art.

Also included within the scope of the invention are polypeptides or unique fragments or derivatives thereof that are differentially modified during or after translation, e.g., by phosphorylation, glycosylation, crosslinking, acylation, proteolytic cleavage, linkage to an antibody molecule, membrane molecule or other ligand, (Ferguson, et al., Ann. Rev. Biochem. 57:285-320, 1988).

A molecule containing a mutation relative to the wild-type is also contemplated. Preferably the molecule is an isolated and purified DNA molecule. Preferably, the mutation will effect a function of the encoded protein. These can be determined by simple assays. Many types of mutations such as frame-shift and stop mutations can be determined just be sequencing.

Polypeptide fragments of the invention can be produced, for example, by expressing cloned nucleotide sequences of the invention encoding partial polypeptide sequences. Alternatively, polypeptide fragments of the invention can be generated directly from intact polypeptides. Polypeptides can be specifically cleaved by proteoltic enzymes, including, but not limited to, trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine. Alternate sets of cleaved polypeptide fragments are generated by preventing cleavage at a site which is susceptible to a proteolytic enzyme. For example, reaction of the ε-amino groups of lysine with ethyltrifluorothioacetate in mildly basic solution yields a blocked amino acid residue whose adjacent peptide bond is no longer susceptible to hydrolysis by trypsin. Goldberger et al. Biochem., 1:401 (1962). Treatment of such a polypeptide with trypsin thus cleaves only at the arginyl residues.

Polypeptides also can be modified to create peptide linkages that are susceptible to proteolytic enzyme catalyzed hydrolysis. For example, alkylation of cysteine residues with β-halo ethylamines yields peptide linkages that are hydrolyzed by trypsin. Lindley, Nature, 178: 647 (1956). In addition, chemical reagents that cleave polypeptide chains at specific residues can be used. Withcop, Adv. Protein Chem. 16: 221 (1961). For example, cyanogen bromide cleaves polypeptides at methionine residues. Gross & Witkip, J. Am Chem Soc., 83: 1510 (1961). Thus, by treating MSH5 polypeptides or fragments thereof with various combinations of modifiers, proteolytic enzymes and/or chemical reagents, numerous discrete overlapping peptides of varying sizes are generated. These peptide fragments can be isolated and purified from such digests by chromatographic methods.

Alternatively, polypeptides of the present invention can be synthesized using an appropriate solid state synthetic procedure. Steward and Young, *Solid Phase Peptide Synthesis*, Freemantle, San Francisco, Calif. (1968). A preferred method is the Merrifield process. Merrifield, *Recent Progress in Hormone Res.*, 23: 451 (1967). The activity of these peptide fragments may conveniently be tested using, for example, a filter binding or immunologic assay as described herein.

Also within the scope of the invention are nucleic acid sequences or proteins encoded by nucleic acid sequences derived from the same gene but lacking one or more structural features as a result of alternative splicing of transcripts from a gene that also encodes the complete mismatch repair gene, as defined previously.

Nucleic acid sequences complementary to DNA or RNA sequences encoding polypeptides of the invention or a functionally active portion(s) thereof are also provided. In animals, particularly transgenic animals, RNA transcripts of a desired gene or genes may be translated into polypeptide products having a host of phenotypic actions. In a particular aspect of the invention, antisense oligonucleotides can be synthesized. These oligonucleotides may have activity in their own right, such as antisense reagents which block translation or inhibit RNA function. Thus, where human polypeptide is to be produced utilizing the nucleotide sequences of this invention, the DNA sequence can be in an inverted orientation which gives rise to a negative sense (Aantisense") RNA on transcription. This antisense RNA is not capable of being translated to the desired product, as it is in the wrong orientation and would give a nonsensical product if translated.

Nucleotide Hybridization Probes

The present invention also provides an isolated nucleotide "probe" that is capable of hybridizing to a eukaryotic target sequence that is homologous to a bacterial mismatch repair gene.

A probe is a ligand of known qualities that can bind selectively to a target. A nucleotide probe according to the invention is a strand of nucleic acid having a nucleotide sequence that is complementary to a nucleotide sequence of a target strand. In particular, the nucleotide sequence of a probe of the present invention is complementary to a sequence found in a mammalian MSH5 nucleotide sequence. In particular, probes that hybridize to any unique segment of any of SEQ ID NO.:1 are included in the invention. Such probes are useful, for example, in nucleic acid hybridization assays, Southern and Northern blot analyses, etc. Hybridization conditions can vary depending on probe length and compositions. Conditions appropriate to a particular probe length and composition can be readily determined by consultation with standard reference materials (see Sambrook et al. supra).

A preferred oligonucleotide probe typically has a sequence somewhat longer than that used for the PCR primers. A longer sequence is preferable for the probe, and it is valuable to minimize codon degeneracy. A representative protocol for the preparation of an oligonucleotide probe for screening a cDNA library is described in Sambrook, J. et al., Molecular Cloning, Cold Spring Harbor Press, New York, 1989. In general, the probe is labeled, e.g., $^{32}$P, and used to screen clones of a cDNA or genomic library.

Preferred nucleotide probes are at least 20-30 nucleotides long, and contain at least 15-20 nucleotides that are complimentary to their target sequence in a eukaryotic nucleotide sequence that is homologous to a bacterial mismatch repair gene. Preferably, they contain at least 17 contiguous MSH5 nucleotides. More preferably, at least 20 contiguous MSH5 nucleotides. Preferred nucleotide probes can be radioactively labeled or conjugated to fluorescent tags such as those available from New England Biolabs (Beverly, Mass.) or Amersham (Arlington Heights, Ill.) and can be used to probe, for example, Southern blots, Northern blots, plaque lifts, colony lifts, etc. Nucleotide probes of the invention include, for example, probes made by chemical synthesis and probes generated by PCR.

Preferred nucleotide probes of the invention, be they oligonucleotides, PCR—generated fragments, or other nucleic acid sequences (e.g. isolated clones), can be used in the general protocol described above.

Nucleotide probes of the invention can also be used in standard procedures such as nick translation, 5' end labeling and random priming (Sambrook et al. supra).

Antibodies

The term "antibodies" is meant to include monoclonal antibodies, polyclonal antibodies and antibodies prepared by recombinant nucleic acid techniques that are selectively reactive with polypeptides encoded by eukaryotic nucleotide sequences of the present invention. The term Aselectively reactive@ refers to those antibodies that react with one or more antigenic determinants of a MSH5 polypeptide and do not react to any appreciable extent with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes.

In particular, antibodies may be raised against amino-terminal (N-terminal) or carboxy-terminal (C-terminal) peptides of a polypeptide encoded by MSH5 nucleotide sequences.

Generally, to isolate antibodies to a MSH5 polypeptide of the invention, a peptide sequence that contains an antigenic determinant is selected as an immunogen. This peptide immunogen can be attached to a carrier to enhance the immunogenic response. Although the peptide immunogen can correspond to any portion of such a polypeptide, certain amino acid sequences are more likely than others to provoke an immediate response, for example, an amino acid sequence including the C-terminal amino acid of a polypeptide encoded by a gene that contains nucleotide sequences of the invention.

Other alternatives to preparing antibodies that are reactive with a polypeptide encoded by a human nucleotide sequence of the invention include: (i) immunizing an animal with a protein expressed by a prokaryotic (e.g., bacterial) or eukaryotic cell; the cell including the coding sequence for all or part of a MSH5 polypeptide; or (ii) immunizing an animal with whole cells that are expressing all or a part of a MSH5 polypeptide. For example, a cDNA clone encoding a polypeptide of the present invention may be expressed in a host using standard techniques (see above; see Sambrook et al., Molecular Cloning; A Laboratory Manual, Cold Spring Harbor Press, Cold Spring Harbor, N.Y.: 1989) such that 5-20% of the total protein that can be recovered from the host is the MSH5 polypeptide. Recovered proteins can be electrophoresed using PAGE and the appropriate protein band can be cut out of the gel. The desired protein sample can then be eluted from the gel slice and prepared for immunization. Alternatively, a protein of interest can be purified by using conventional methods such as, for example, ion exchange hydrophobic, size exclusion, or affinity chromatography.

Once the protein immunogen is prepared, mice can be immunized twice intraperitoneally with approximately 50 micrograms of protein immunogen per mouse. Sera from such immunized mice can be tested for antibody activity by immunohistology or immunocytology on any host system expressing a polypeptide encoded by eukaryotic nucleotide sequence that is homologous to a bacterial mismatch repair gene and by ELISA with the expressed polypeptide encoded by a eukaryotic nucleotide sequence that is homologous to a bacterial mismatch repair gene. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

To further improve the likelihood of producing an antibody as provided by the invention, the amino acid sequence of MSH5 polypeptides may be analyzed in order to identify portions of amino acid sequence which may be associated with increased immunogenicity. For example, polypeptide sequences may be subjected to computer analysis to identify potentially immunogenic surface epitopes. Such computer analysis can include generating plots of antigenic index, hydrophilicity, structural features such as amphophilic helices or amphophilic sheets and the like.

For preparation of monoclonal antibodies directed toward polypeptides encoded by a eukaryotic nucleotide sequence of the invention, any technique that provides for the production of antibody molecules by continuous cell lines may be used. For example, the hybridoma technique originally developed by Kohler and Milstein (Nature, 256: 495-497, 1973), as well as the trioma technique, the human B-cell hybridoma technique (Kozbor et al., Immunology Today, 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al. U.S. Pat. Nos. 4,704,694 and 4,976,778).

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to antibodies against polypeptides encoded by a eukaryotic nucleotide sequence that is homologous to a bacterial mismatch repair gene, or to other molecules of the invention. See, for example, A Conjugate Vaccines," Contributions to Microbiology and Immunology, J. M. Cruse and R. E. Lewis, Jr (eds), Carger Press, New York, (1989), the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, ASpecific killing of lymphocytes that cause experimental Autoimmune Myesthenia Gravis by toxin-acetylcholine receptor conjugates." Jour. Immun. 133:1335-2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. AImmunotoxins: Hybrid molecules combining high specificity and potent cytotoxicity@. Immunological Reviews 62:185-216; and Vitetta et al., supra).

Preferred linkers are described in the literature. See, for example, Ramakrishnan, S. et al., Cancer Res. 44:201-208 (1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. #21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Antibodies of the present invention can be detected by any of the conventional types of immunoassays. For example, a sandwich assay can be performed in which a polypeptide encoded by a eukaryotic nucleotide sequence that is homologous to a bacterial mismatch repair gene, as provided by the invention, is affixed to a solid phase. A liquid sample such as kidney or intestinal fluid containing, or suspected of containing, antibodies directed against a such a polypeptide of the invention is incubated with the solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide of the present invention is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid and the label bound to the solid phase is measured, the amount of the label detected serving as a measure of the amount of anti-urea transporter antibody present in the sample. These and other immunoassays can be easily performed by those of ordinary skill in the art.

Definitions gene—The term "gene", as used herein, refers to a nucleotide sequence that contains a complete coding sequence. Generally, "genes" also include nucleotide sequences found upstream (e.g. promoter sequences, enhancers, etc.) or downstream (e.g. transcription termination signals, polyadenylation sites, etc.) of the coding sequence that affect the expression of the encoded polypeptide.

wild-type—The term "wild-type", when applied to nucleic acids and proteins of the present invention, means a version of a nucleic acid or protein that functions in a manner indistinguishable from a naturally-occurring, normal version of that nucleic acid or protein (i.e. a nucleic acid or protein with wild-type activity). For example, a "wild-type" allele of a mismatch repair gene is capable of functionally replacing a normal, endogenous copy of the same gene within a host cell without detectably altering mismatch repair in that cell. Different wild-type versions of the same nucleic acid or protein may or may not differ structurally from each other.

non-wild type—The term "non-wild-type" when applied to nucleic acids and proteins of the present invention, means a version of a nucleic acid or protein that functions in a manner distinguishable from a naturally-occurring, normal version of that nucleic acid or protein. Non-wild-type alleles of a nucleic acid of the invention may differ structurally from wild-type alleles of the same nucleic acid in any of a variety of ways including, but not limited to, differences in the amino acid sequence of an encoded polypeptide and/or differences in expression levels of an encoded nucleotide transcript or polypeptide product.

For example, the nucleotide sequence of a non-wild-type allele of a nucleic acid of the invention may differ from that of a wild-type allele by, for example, addition, deletion, substitution, and/or rearrangement of nucleotides. Similarly, the amino acid sequence of a non-wild-type mismatch repair protein may differ from that of a wild-type mismatch repair protein by, for example, addition, deletion, substitution, and/or rearrangement of amino acids.

Particular non-wild-type nucleic acids or proteins that, when introduced into a normal host cell, interfere with the endogenous mismatch repair pathway, are termed "dominant negative" nucleic acids or proteins.

homologous/homologue—The term "homologous", as used herein is an art-understood term that refers to nucleic acids or polypeptides that are highly related at the level of nucleotide or amino acid sequence. Nucleic acids or polypeptides that are homologous to each other are termed "homologues".

The term "homologous" necessarily refers to a comparison between two sequences. In accordance with the invention, two nucleotide sequences are considered to be homologous if the polypeptides they encode are at least about 50-60% identical, preferably about 70% identical, for at least one stretch of at least 20 amino acids. Preferably, homologous nucleotide sequences are also characterized by the ability to encode a stretch of at least 4-5 uniquely specified amino acids. Both the identity and the approximate spacing of these amino acids relative to one another must be considered for nucleotide sequences to be considered to be homologous. For nucleotide sequences less than 60 nucleotides in length, homology is determined by the ability to encode a stretch of at least 4-5 uniquely specified amino acids.

upstream/downstream—The terms "upstream" and "downstream" are art-understood terms referring to the position of an element of nucleotide sequence. "Upstream" signifies an element that is more 5' than the reference element. "Downstream" refers to an element that is more 3' than a reference element.

intron, exon/intron—The terms "exon" and "intron" are art-understood terms referring to various portions of genomic gene sequences. "Exons" are those portions of a genomic gene sequence that encode protein. "Introns" are sequences of nucleotides found between exons in genomic gene sequences.

sporadic—The term "sporadic" as used herein and applied to tumors or cancers, refers to tumors or cancers that arise in an individual not known to have a genetic or familial pre-disposition to cancer. The categorization of a tumor or cancer as "sporadic" is, of necessity, based on available information and should be interpreted in that context. It is possible, for example, that an individual that inherits a low-penetrance mutation (i.e. a mutation that, statistically, is unlikely to have a dramatic phenotype) will develop cancer as a result of that mutation (i.e. will have had a genetic pre-disposition to cancer) but will have had no family history of cancer. Tumors in that individual might originally be identified as sporadic because the individual was not known to have a genetic predisposition to cancer. The term "sporadic", therefore, is used to conveniently describe those tumors or cancers that appear to have arisen independent of inherited genetic motivation, but is not intended to point to defining molecular distinctions between inherited and sporadic tumors or cancers.

affected—The term "affected", as used herein, refers to those members of a kindred that either have developed a characteristic cancer and/or are predicted, on the basis of, for example, genetic studies, to carry an inherited mutation that confers susceptibility to cancer.

The invention will now be further described in the following examples.

Cloning and Characterization of the Human MSH5 Gene

The original human EST (clone i.d. 115902) was identified by homology searches of the dbEST using the hMSH2 amino acid sequence. The sequence of this clone was determined from T3 and T7 primers. The 992 bp contig generated showed homology when translated and aligned with S. cerevisiae MSH5. The original contig corresponds to bp 1908-2900 of the complete cDNA. The 5=end of the cDNA was then cloned in two consecutive 5=RACE steps. The 3=end was confirmed by 3=RACE.

The human genomic locus was cloned by screening a P1 human genomic DNA library by PCR using primers DFCI 23663 (SEQ ID NO:51)(GAATGGCAGACATCCTCTGA) and DFCI 23876 (SEQ ID NO:52)(GGTATATGCTCTTC-CCTGATGA). The intron-exon junctions of hMSH5 were characterized by sequencing these clones using primers derived from the hMSH5 cDNA sequence.

HMSH5 was mapped unambiguously to chromosome 6 by PCR analysis of the NIGMS Human/Roden Somatic Cell Hybrid Mapping Panel 2. Alternative locations of chromosome 1 or 6 had been obtained. Subsequent demonstration that the chromosome 1-specific NIGMS line was actually contaminated with DNA from the chromosome 6-specific line confirmed the location of the gene on human chromosome 6. Fine mapping to 6p21.3 was completed and reconfirmed by PCR analysis of a radiation hybrid panel. The actual result was: 7.04 cR from CHLC.GATA4A03.76, at a LOD score of >3. The mapping panel used was Genebridge 4, obtained from Research Genetics, Inc.

The Complete cDNA Sequence for hMSH5

CGCTCCTTTTGCAGGCTCGTGGCGGTCGGTCAGCGGGCGTTCTCCCACCTGTAGCGACTCAGGTTACTGAAAAGGCGGGAAAACGCTGC (SEQ ID NO:1)

GATGGCGGCAGCTGGGGGAGGAGGAAGATAAGCGCGTGAGGCTGGGGTCCTGGCGCGTGGTTGGCAGAGGCAGAGACATAAGACGTGCAC

```
GACTCGCCCCACAGGGCCTTCAGACCCCTTCTTTCCAAAGGAGCCTCCAAGCTCATGGCCTCCTTAGGAGCGAACCCAAGGAGGACACCG
CAGGGACCGAGACCTGGGGCGGCCTCCTCCGGTTTCCCCAGCCCGGCCCCAGTGCCGGGCCCCAGGGAGGCCGAGGAGGAGGAAGTCGAG
GAGGAGGAGGAGCTGGCCGAGATCCATCTGTGTGTGCTGTGGAATTCAGGATACTTGGGCATTGCCTACTATGATACTAGTGACTCCACT
ATCCACTTCATGCCAGATGCCCCAGACCACGAGAGCCTCAAGCTTCTCCAGAGAGTTCTGGATGAGATCAATCCCCAGTCTGTTGTTACG
AGTGCCAAACAGGATGAGAATATGACTCGATTTCTGGGAAAGCTTGCCTCCCAGGAGCACAGAGAGCCTAAAAGACCTGAAATCATATTT
TTGCCAAGTGTGGATTTTGGTCTGGAGATAAGCAAACAACGCCTCCTTTCTGGAAACTACTCCTTCATCCCAGACGCCATGACTGCCACT
GAGAAAATCCTCTTCCTCTCTTCCATTATTCCCTTTGACTGCCTCCTCACAGTTCGAGCACTTGGAGGGCTGCTGAAGTTCCTGGGTCGA
AGAAGAATCGGGGTTGAACTGGAAGACTATAATGTCAGCGTCCCCATCCTGGGCTTTAAGAAATTTATGTTGACTCATCTGGTGAACATA
GATCAAGACACTTACAGTGTTCTACAGATTTTTAAGAGTGAGTCTCACCCCTCAGTGTACAAAGTGGCCAGTGGACTGAAGGAGGGGCTC
AGCCTCTTTGGAATCCTCAACAGATGCCACTGTAAGTGGGGAGAGAAGCTGCTCAGGCTATGGTTCACACGTCCGACTCATGACCTGGGG
GAGCTCAGTTCTCGTCTGGACGTCATTCAGTTTTTTCTGCTGCCCCAGAATCTGGACATGGCTCAGATGCTGCATCGGCTCCTGGGTCAC
ATCAAGAACGTGCCTTTGATTCTGAAACGCATGAAGTTGTCCCACACCAAGGTCAGCGACTGGCAGGTTCTCTACAAGACTGTGTACAGT
GCCCTGGGCCTGAGGGATGCCTGCCGCTCCCTGCCGCAGTCCATCCAGCTCTTTCGGGACATTGCCCAAGAGTTCTCTGATGACCTGCAC
CATATCGCCAGCCTCATTGGGAAAGTAGTGGACTTTGAGGGCAGCCTTGCTGAAAATCGCTTCACAGTCCTCCCCAACATAGATCCTGAA
ATTGATGAGAAAAAGCGAAGACTGATGGGACTTCCCAGTTTCCTTACTGAGGTTGCCCGCAAGGAGCTGGAGAATCTGGACTCCCGTATT
CCTTCATGCAGTGTCATCTACATCCCTCTGATTGGCTTCCTTCTTTCTATTCCCCGCCTGCCTTCCATGGTAGAGGCGACTTCATGTTCT
CTCAGAGGAGAAGCTGCACTATCGTAGTGCCCGAACCAAGGAGCTGGATGCATTGCTGGGGGACCTGCACTGCGAGATCCGGGACCAGGA
GACGCTGCTGATGTACCAGCTACAGTGCCAGGTGCTGGCACGAGCAGCTGTCTTAACCCGAGTATTGGACCTTGCCTCCCGCCTGGACGT
CCTGCTGGCTCTTGCCAGTGCTGCCCGGGACTATGGCTACTCAAGGCCGCGTTACTCCCCACAAGTCCTTGGGGTACGAATCCAGAATGG
CAGACATCCTCTGATGGAACTCTGTGCCCGAACCTTTGTGCCCAACTCCACAGAATGTGGTGGGGACAAAGGGAGGGTCAAAGTCATCAC
TGGACCCAACTCATCAGGGAAGAGCATATACCTCAAACAGGTAGGCTTGATCACATTCATGGCCCTGGTAGGCAGCAGTTTGTGCCAGCA
GAGGAGGCCGAAATTGGGGCAGTAGACGCCATCTTCACACGAATTCATAGCTGCGAATCCATCTCCCTTGGCCTCTCCACCTTCATGATC
GACCTCAACCAGGTGGCGAAAGCAGTGAACAATGCCACTGCACAGTCGCTGGTCCTTATTGATGAATTTGGAAAGGGAACCAACACGGTG
GATGGGCTCGCGCTTCTGGCCGCTGTGCTCCGACACTGGCTGGCACGTGGACCCACATGCCCCACATCTTTGTGGCCACCAACTTTCTG
AGCCTTGTTCAGCTACAACTGCTGCCACAAGGGCCCCTGGTGCAGTATTTGACCATGGAGACCTGTGAGGATGGCAACGATCTTGTCTTC
TTCTATCAGGTTTGCGAAGGTGTTGCGAAGGCCAGCCATGCCTCCCACACAGCTGCCCAGGCTGGGCTTCCTGACAAGCTTGTGGCTCGT
GGCAAGGAGGTCTCAGATTTGATCCGCAGTGGAAAACCCATCAAGCCTGTCAAGGATTGCTAAAGAAGAACCAAATGGAAAATTGCCAGA
CATTAGTGGATAAGTTTATGAAACTGGATTTGGAAGATCCTAACCTGGACTTGAACGTTTTCATGAGCCAGGAAGTGCTGCCTGCTGCCA
CCAGCATCCTCTGAGAGTCCTTCCAGTGTCCTCCCCAGCCTCCTGAGACTCCGGTGGGCTGCCATGCCCTCTTTGTTTCCTTATCTCCCT
CAGACGCAGAGTTTTTAGTTTCTCTAGAAATTTTGTTTCATATTAGGAATAAAGTTTATTTTGAAGAAAAAAAAAAAAAAAAAA
```

The cDNA is 2881 bp, exclusive of the poly-A tail. The translational start is base 235 (A of ATG). The translational stop is base 2737 (T of TGA).

hMSH5 Predicted Amino Acid Sequence

```
MASLGANPRRTPQGPRPGAASSGFPSPAPVPGPREAE    (SEQ ID NO:2)

EEEVEEEELAEIHLCVLWNSGYLGIAYYDTSDSTIH

FMPDAPDHESLKLLQRVLDEINPQSVVTSAKQDENMT

RFLGKLASQEHREPKRPEIIFLPSVDFGLEISKQRLL

SGNYSFIPDAMTATEKILFLSSIIPFDCLLTVRALGG

LLKFLGRRRIGVELEDYNVSVPILGFKKFMLTHLVNI

DQDTYSVLQIFKSESHPSVYKVASGLKEGLSLFGILN

RCHCKWGEKLLRLWFTRPTHDLGELSSRLDVIQFFLL

PQNLDMAQMLHRLLGHIKNVPLILKRMKLSHTKVSDW

QVLYKTVYSALGLRDACRSLPQSIQLFRDIAQEFSDD

LHHIASLIGKVVDFEGSLAENRFTVLPNIDPEIDEKK

RRLMGLPSFLTEVARKELENLDSRIPSCSVIYIPLIG

FLLSIPRLPSMVEASDFEINGLDFMFLSEEKLHYRSA

RTKELDALLGDLHCEIRDQETLLMYQLQCQVLARAAV
```

-continued

LTRVLDLASRLDVLLALASAARDYGYSRPRYSPQVLG

VRIQNGRHPLMELCARTFVPNSTECGGDKGRVKVITG

PNSSGKSIYLKQVGLITFMALVGSFVPAEEAEIGAVD

AIFTRIHSCESISLGLSTFMIDLNQVAKAVNNATAQS

LVLIDEFGKGTNTVDGLALLAAVLRHWLARGPTCPHI

FVATNFLSLVQLQLLPQGPLVQYLTMETCEDGNDLVF

FYQVCEGVAKASHASHTAAQAGLPDKLVARGKEVSDL

IRSGKPIKPVKDLLKKNQMENCQTLVDKFMKLDLEDP

NLDLNVFMSQEVLPAATSIL

Sequences of the hMSH5 Intron-exon Junctions

The tildes (~) indicate approximate intron size, estimated by PCR across the introns. The combined size for introns 9 and 10 (*) is ~2200 bp, as individual size estimates were not made in this case. Introns without tildes were completely sequenced. Additional intronic sequences generated to date are included in Appendix I.

The coding sequence (end of exon adjacent to each border) is in capitals and the intronic sequence is lowercase. Consensus splice donor and acceptor sequences are in bold. Phase indicates border phase, which means that the border falls after the indicated base of a codon. For example, given a methionine (ATG) codon: phase of 1 means the border falls between A and T, phase of 2 means the border falls between T and G, while phase of 3 means the border follows the codon. The first intron is in the 5? UTR. Therefore, phase is not applicable.

H5 Gene Structure

| INTRON # | phase | length (bp) | 5' border: | | SEQ ID NO: |
|---|---|---|---|---|---|
| 1 | NA | 232 | TTCCAAAGG | gtaacctccgcgtgacagaa | 3 |
| 2 | 3~600 | | CTGGCCGAG | gtctctgaggggagtagaaa | 4 |
| 3 | 1~1500 | | TCCAGAGAG | gtggggatggaaccatgaat | 5 |
| 4 | 1150 | | GAAAGCTTG | gtaaggacttggtaaaggat | 6 |
| 5 | 1733 | | TGGATTTTG | gtatctccttccttttgctt | 7 |
| 6 | 3164 | | CTCCTCACA | gtgagattggtcctggggga | 8 |
| 7 | 2246 | | ATTTATGTT | gtaggtgattcaccccaacc | 9 |
| 8 | 2~626 | | CACTTACAG | gtaaagaggtggaggcatgc | 10 |
| 9 | 1* | | GCCTCTTTG | gtaggtgtgcccatccctc | 11 |
| 10 | 2~2200* | | GCTGCTCAG | gtgagtgggtcccacacata | 12 |
| 11 | 3127 | | AACGTGCCT | gtgagcccagggtggaggc | 13 |
| 12 | 3~594 | | CTCTACAAG | gtaaggccttccttcttgaa | 14 |
| 13 | 3254 | | GGGAAAGTA | gtgagtagaaggaaaaaggg | 15 |
| 14 | 1145 | | TTGATGAGA | gtgagtgtgggtgtggatg | 16 |
| 15 | 3~267 | | ATCCCTCTG | gtgagggcaggagagtgggt | 17 |
| 16 | 3247 | | GACTTCATG | gtaagaccctcaacctctgt | 18 |
| 17 | 1273 | | AGATCCGGG | gtgaggaaaagccagaggtt | 19 |
| 18 | 2114 | | GAATGGCAG | gtaagaatagaggcgggtgg | 20 |
| 19 | 3473 | | CTCAAACAG | gtgaggagaagccctgcagc | 21 |
| 20 | 3348 | | CTCAACCAG | gtcaaagggaacaaagggag | 22 |
| 21 | 3209 | | ACCAACACG | gtgaggggagaaactgatga | 23 |
| 22 | 3202 | | CAGTATTTG | gtgaggagaccaatctagct | 24 |
| 23 | 3155 | | GGCAAGGAG | gtgatgagatccaaatgtgc | 25 |
| 24 | 2234 | | AATGGAAAA | gtgcgtatatggccccagtg | 26 |

-continued

| INTRON # | phase | length (bp) | 5' border: | | SEQ ID NO: |
|---|---|---|---|---|---|
| 1 | NA232 | ctcacttttgcatccgcag | AGCCTCCAA | | 27 |
| 2 | 3~600 | ctttcttccttgctggacag | ATCCATCTG | | 28 |
| 3 | 1~1500 | gatctctgttctccttccag | TTCTGGATG | | 29 |
| 4 | 1150 | ttttctttcctcccccacag | CCTCCCAGG | | 30 |
| 5 | 1733 | tgcttgcctccctcaaatag | GTCTGGAGA | | 31 |
| 6 | 3164 | cactgctgatcccctcccag | GTTCGAGCA | | 32 |
| 7 | 2246 | ttttgttttctgtcctcag | GACTCATCT | | 33 |
| 8 | 2~626 | cctccatttctcctcgacag | TGTTCTACA | | 34 |
| 9 | 1* | cctgccttatccctcacaag | AATCCTCAA | | 35 |
| 10 | 2~2200* | acccaaaccctcacttccag | GCTATGGTT | | 36 |
| 11 | 3127 | gtaaccttgtctgactgtag | TTGATTCTG | | 37 |
| 12 | 3~594 | ttttgtgtttctctcacag | ACTGTGTAC | | 38 |
| 13 | 3254 | aacagtacttatctcctcag | GTGGACTTT | | 39 |
| 14 | 1145 | cctgtcttccaccctcgtag | AAAAGCGAA | | 40 |
| 15 | 3~267 | ctcctctttactctccccag | ATTGGCTTC | | 41 |
| 16 | 3247 | ctttgaaccctgtacccag | TTTCTCTCA | | 42 |
| 17 | 1273 | ccttcctcacccactcccag | ACCAGGAGA | | 43 |
| 18 | 2114 | tgcctctccgcccactgcag | ACATCCTCT | | 44 |
| 19 | 3473 | ctgtctccttccctattcag | GTAGGCTTG | | 45 |
| 20 | 3348 | gtccaccttatacccagcag | GTGGCGAAA | | 46 |
| 21 | 3209 | aacctctgccctctttgcag | GTGGATGGG | | 47 |
| 22 | 3202 | gtcttttattctcttttaag | ACCATGGAG | | 48 |
| 23 | 3155 | caccttcttgcttgtcctag | GTCTCAGAT | | 49 |
| 24 | 2234 | cgattttctctcttcttcag | TTGCCAGAC | | 50 |

There are 25 exons in the human gene. Their sizes (in bp) are as follows:
1. 221
2. 160
3. 124
4. 81
5. 63
6. 122
7. 110
8. 36
9. 83
10. 46
11. 139
12. 63
13. 129
14. 73
15. 110
16. 81
17. 88
18. 190
19. 127
20. 150
21. 75
22. 144
23. 138
24. 74
25. 254

The estimated size of the hMSH5 gene is 12,974 bp.

Cloning and Characterization of the Mouse MSH5

The original segment of the mouse MSH5 gene was obtained by genomic PCR using primers DFCI 24781 (SEQ ID NO:101) (CCAGAACTCTCTGGAGAAGC) and DFCI 24931 (SEQ ID NO:102)(GTGCTGTGGAATTCAG-GATAC), based on the human cDNA sequence. The sequence of the mouse genomic PCR product was determined from the same primers. The resulting 76 bp sequence exhibited three nucleotide substitutions relative to the human sequence. The nucleotide substitutions were conservative (none was predicted to alter the amino acid sequence of the mouse protein relative to the human protein). The original genomic PCR product corresponds to bp 213-330 of the attached mouse cDNA. The 5=end of the cDNA was then cloned by 5=RACE, using this sequence as a starting point.

The 3=end was cloned by RTPCR using primers DFCI NJW100 (SEQ ID NO:103) (CTCCACTATCCACTTCATGCCAGATGC) and DFCI 23924 (SEQ ID NO:104) (GCTGGGGAGGACACTGGAAGGACTCTCA) after 3=RACE products generated with DFCI NJW100 proved refractory to cloning.

The mMSH5 genomic locus was cloned by screening a P1 mouse embryonic stem cell genomic DNA library by PCR using primers DFCI 24781 (SEQ ID NO:101) (CCAGAACTCTCTGGAGAAGC) and DFCI 24931 (SEQ ID NO:102) (GTGCTGTGGAATTCAGGATAC).

Several intron-exon junctions of mMSH5 were determined by sequencing of these clones using primers derived from the mMSH5 cDNA sequence. MMSH5 intronic sequences generated to date are set forth below.

The chromosomal location of mMSH5 has not been experimentally determined. However, based on comparative mapping data for human and mouse chromosomes, we predict that mMSH5 is located on mouse chromosome 17 in the syntenic region containing the murine homologues of C2, C4, $Tnf^{\alpha}$ and HLA.B, which flank, or are closely associated with, the hMSH5 locus in 6p21.3.

The mMSH5 cDNA Sequence

```
GGCTTGGGGCGGTTGGTCAGGGAGGTGGATCGTCGCGGCTGAGAGTCGCCGAGCCCATGGCTTTCAGAGCGACCCCAGGCCGGACGCC  (SEQ ID NO:53)
GCCGGGACCCGGACCCAGATCCGGAATCCCCTCAGCCAGCTTCCCCAGCCCTCAGCCCCCAATGGCGGGGCCTGGAGGTATCGAGGAA
GAGGACGAGGAGGAGCCCGCCGAGATCCATCTGTGCGTGCTGTGGAGCTCGGGATACCTGGGCATTGCTTACTATGACACTAGTGACT
CCACTATCCACTTCATGCCAGATGCCCCAGACCACGAGAGCCTAAAGCTTCTCCAGAGAGTTCTGGATGAAATCAACCCCCAGTCTGT
TGTCACAAGTGCCAAACAGGATGAGGCTATGACTCGATTTCTAGGGAAGCTTGCCTCTGAGGAGCACAGAGAGCCAAAGGGACCTGAA
ATCATACTTCTGCCAAGCGTGGATTTTGGTCCAGAGATAAGCAAACAGCGTCTCCTTTCCGGAAACTACTCCTTCATCTCAGACTCCA
TGACTGCTACTGAGAAAATCCTTTTCCTCTCCTCCATTATTCCCTTTGACTGTGTCCTCACGGTCCGGGCATCAAGTTCCTGAGTCGA
AGAAGAATTGGGGTTGAACTGGAAGACTATGATGTTGGCGTCCCTATCCTGGGATTCAAGAAGTTTGTATTGACCCATCTGGTGAGCA
TAGATCAAGACACTTACAGCGTTCTACAGATTTTCAAGAGTGAGTCTCACCCCTCGGTGTACAAAGTAGCCAGTGGGCTGAAGGAGGG
GCTCAGCCTTTTTGGAATCCTCAACAGATGCCGCTGTAAGTGGGGACAGAAGCTGCTCAGGCTGTGGTTTACACGTCCAACCCGGGAG
CTAAGGGAACTCAATTCCCGACTGGATGTCATTCAGTTCTTCCTGATGCCTCAGAACCTGGACATGGCCCAGATGCTGCACCGACTCC
TGAGCCACATCAAGAATGTGCCTCTGATTCTGAAACGCATGAAGTTGTCCCACACCAAGGTCAGTGACTGGTGTACAGTGCTCTCGGC
CTGAGGGATGCCTGCCGTTCTCTGCCACAGTCCATCCAGCTTTTTCAGGACATTGCCCAGGAGTTCTCTGACGACCTGCATCACATTG
CCAGCCTCATCGGGAAGGTGGTGGACTTTGAGGAAAGTCTTGCTGAAAATCGCTTCACAGTCCTCCCTAACATAGACCCTGACATAGA
TGCCAAGAAGCGAAGGCTGATAGGGCTTCCGAGCTTCCTCACTGAAGTTGCTCAGAAGGAGCTGGAGAACCTGGACTCTCGCATCCCC
TCATGCAGTGTCATCTACATCCCTCTGATTGGCTTCCTTCTTTCCATTCCCCGCTTGCCTTTCATGGTGGAAGCTAGTGACTTTGAGA
TTGAGGGGCTGGACTTCATGTTTCTCTCAGAGGACAAGCGCACTATCGTAGCGCCCGGAcCAAGGAGCTGTGCACTGTGAGATCCGGG
ACCAGGAGACTCTGTTGATGTACCAGCTGCAGTGCCAGGTGCTGGCACGGGCTTCGGTCTTGACTCGGGTATTGGACCTTGCCTCCCG
CCTGGACGTCTTGTTGGCTCTTGCCAGTGCTGCCCGGGACTACGGCTTATTCGAGACCGCATTACTCTCCCTGTATCCATGGAGTACG
AATCAGGAATGGCAGGCATCCTCTGATGGAACTGTGTGCACGAACCTTCGTGCCCAACTCCACGGACTGTGGTGGGGACCAGGGCAGG
GTCAAAGTCATCACTGGACCCAACTCCTCAGGGAAAAGCATATATCTCAAGCAGGTAGGCTTGATCACTTTCATGGCCCTGGTGGGCA
GTTTCGTGCCTGCAGAGGAGGCCGAGATTGGGGTAATCGACGCCATCTTCACTCGAATTCACAGCTGCGAATCCATCTCCCTCGGCCT
cTCCACCTTCATGATTGATCTCAACCAGGTGGCGAAAGCAGTGAACAATGCCACAGAGCACTCGCTGGTCCTGATCGATGAATTCGGG
AAGGGGACCAACTCGGTGGATGGCCTGGCACTTCTGGCTGCTGTGCTCCGTCACTGGCTTGCACTGGGACCCAGCTGCCCCACGTCT
TTGTAGCCACCAACTTCCTGAGCCTTGTTCAGCTGCAGCTGCTGCCGCAAGGACCCCTGGTGCAGTATTTGACCATGGAGACTTGTGA
GGATGGGAAGACCTTGTCTTCTTCTACCAGCTTTGCCAAGGCGTCGCCAGTGCCAGCCACGCCTCCCACACAGCGGCCCAGGCTGGG
CTTCCTGTCAGACTTGATCCGCAGTGGGAAACCCATCAAGGCCACGAATGAGCTTCTAAGGAGAAACCAAATGGAAAACTGCCAGGCA
CTGGTGGATAAGTTTCTAAAACTGGACTTGGAGGATCCCACCCTGGACCTGGACATTTTCATTAGTCAGGAAGTGCTGCCCGCTGCTC
CCACCATCCTCTGAGAGTCCTTCCAGTGTCCT
```

The translational start is base 57 (A of ATG). The translational stop is base 2556 (T of TGA). The 5′ UTR is suspected of being artifactually truncated due to premature termination of reverse transcription. The 3′ UTR incomplete because of the cloning strategy used.

The mMSH5 Predicted Amino Acid Sequence

```
MAFRATPGRTPPGPGPRSGIPSASFPSPQPPMAGPG  (SEQ ID NO:54)
GIEEEDEEEPAEIHLCVLWSSGYLGIAYYDTSDSTI
HFMPDAPDHESLKLLQRVLDEINPQSVVTSAKQDEA
MTRFLGKLASEEHREPKGPEIILLPSVDFGPEISKQ
RLLSGNYSFISDSMTATEKILFLSSIIPFDCVLTVR
ALGGLLKFLSRRRIGVELEDYDVGVPILGFKKFVLT
HLVSIDQDTYSVLQIFKSESHPSVYKVASGLKEGLS
LFGILNRCRCKWGQKLLRLWFTRPTRELRELNSRLD
VIQFFLMPQNLDMAQMLHRLLSHIKNVPLILKRMKL
SHTKVSDWQVLYKTVYSALGLRDACRSLPQSIQLFQ
DIAQEFSDDLHHIASLIGKVVDFEESLAENRFTVLP
NIDPDIDAKKRRLIGLPSFLTEVAQKELENLDSRIP
SCSVIYIPLIGFLLSIPRLPFMVEASDFEIEGLDFM
FLSEDKLHYRSARTKELDTLLGDLHCEIRDQETLLM
YQLQCQVLARASVLTRVLDLASRLDVLLALASAARD
YGYSRPHYSPCIHGVRIRNGRHPLMELCARTFVPNS
TDCGGDQGRVKVITGPNSSGKSIYLKQVGLITFMAL
VGSFVPAEEAEIGVIDAIFTRIHSCESISLGLSTFM
IDLNQVAKAVNNATEHSLVLIDEFGKGTNSVDGLAL
LAAVLRHWLALGPSCPHVFVATNFLSLVQLQLLPQG
PLVQYLTMETCEDGEDLVFFYQLCQGVASASHASHT
AAQAGLPDPLIARGKEVSDLIRSGKPIKATNELLRR
NQMENCQALVDKFLKLDLEDPTLDLDIFISQEVLPA
APTIL
```

Sequences of the hMSH5 Introns

Consensus splice donor and acceptor sequences are in bold. Where the complete intronic sequence is unknown, paired slashes in bold (//) indicate the position of the sequence gap.

```
Intron 1:                                                        (SEQ ID NO:55)
gtaacctccgcgtgacagaatgagggtggggcgcgtggagtttcccacaatctgtactttagttaaatacccg agaattcacctcctgtgtccacagctctccacgcccctcagccctgccccgcagccctgtatcagaagtactt agcgctttgcattctgcgcgccaccctaccccggcctcctctgtgaatcgttgcttccgaaccgccctcactt tttgcatccgcag Intron 2:                                                        (SEQ ID NO:56)
Gtctctgagggagtagaaacttgaatggagagttgatgggaatttaaaataaaagagggttgggagccggg

//

(SEQ ID NO:57)
aaaaaaaaacagggttgggaagagctgggcaagtctcttacctcctgagtggctgtttcacattcactaaatg ggggtgatgatgcctatctcagagatttgagaaaatgattaaattatataagacatggtaaaccctacactta tgagtgattctaatagtgatttcctttcttccttgctggacag Intron 3:                                                        (SEQ ID NO:58)
Gtggggatggaaccatgaattcctctgctctctgggattgcagatgtgttacacacacacacacacacaca cacacacacacatatttttttttctagacagagtcttgctctgttacccaggctcaagtgcagtggcgca atcttggctcactgcagcctccacctcctgggttcaagcaattctcctgactcaacctcccgagtagctggga ctacaggcgtgtgccaccacacccagctagttttttgtgtgtgttttagcacagacggtgtttccaccatgtt ggccagggtggtctcaaactcctgaccttgtgatccgcccaccttggcctcctaaagtgctgggactacaggt gtgagtcaccacgcccagccatgttttacttacattaactcacctcactgtctagcatattttgtgttgctgt aaggaaatac//

(SEQ ID NO:59)
ggcgacaaatatatgacgtatttacaatgtttcaggtgcttcagattcagccctgggcaaatcagtcatgt ctgttctccagggggtttacagcctagtgacaacatccagaacatcccacttccctctcaccatcccaccactc ttaactacttttctaaatctcaacttctacctgtgttcccactgtgcagagcactccctactcctagggagga
```

-continued aatgtttttgagaaggagaggggtaggaagaggagggctatgggttttctcttagtcaaagacaaagatcctt taactcatttgatctctgttctccttccaag Intron 4: (SEQ ID NO:60)
gtaaggacttggtaaaggatagagggaaaatggggaaggactaatatatggaatattccaggggctagaatt gggtgagagggagtgtcagacagaggtagaaggactgagatgtaaagaatgatagccttttctttcctccccc acag Intron 5: (SEQ ID NO:61)
gtatctccttcctttgctttgcctaactccctgttccggtgtcccattctttcccccaactctaccttcatc atcacagatctcccctctgccttatgtcatcctaaacctttgtgctcctcatgccctatgacctgtcccccca agatctctcctgctccctaccctttaataatctgcagcttattgggaagcctctgcttaagtcatgtctaggg atgagggcctcccctgaggagtggtgacactttttggacaggttttattgttggaattctccccattaagtt aaagcctttttatcaccaaaccaaaaggcactgcctcagtgacccttattatgatccataaggcacttctataa ctttcctaggtttacaataagaacaggagtgtactatcctaattagatattaaggcattagtgttactagttc tattaataccattattttgaccaaaatcctcaattccagacagatgtctacttttcctcagccatttatcttttc tcaggctgtgctttcagacaagtatctttatattatgtagaataaaaagagaattagactaagagtctgaa aatttggttcttgctctagctttccattaactgcctgtgtgagcttgggcaagtcaaataatctctcttgctt ctattgtctcattcttaaaatggggtgaaaaaattgagctacaagaccgttcccttttgcttgcctccctcaaa tag Intron 6: (SEQ ID NO:62)
gtgagattggtcctgggggataagggctgggaggcggcacaagtgctagggctgaattctgggaggtactggc ctagccctggaaaatagtaactttccctggtgctctgcagcccccaggagatttaagatttaccccgattcca ctgctgatcccctcccag Intron 7: (SEQ ID NO:63)
gtaggtgattcaccccaaccccaaccaaagtaatgtgggattggggaggcctgaaaagtaaagtgggggtgggg tgtggatgtggctgtgacccagtgggtcaagggctctaggacaccccgggagaatctaagggctaatgagactt tgggaagaagactgggacaatattcagagagggggacaaaggaagtggagttgtggaacgaactcagactgct tcctgctttttttgttttctgtcctcag Intron 8: (SEQ ID NO:64)
Gtaaagaggtggaggcatgctgctgtctctggggagggagaaggattaagtttaatgccccaataatcctaat gaggctctagtttccctaatcctggggctattaagatctctctcctgaaggaaagggaagggggggttttgag ggaaagagaggaagaaaagcataaagatactagctttcttttctatagggagaaactgaggcaaagaaaagta agggacaaaccttacatcaagatatgatctcggctgggcgcggtggctcatgcctgtaatccccgcgctttgg gaggccaaggcgggtggatcgcctgaggtcaggagtttgagacctgaccaatatggtaaaacccccgtctctac taaaaatataaaaattagctgggtgtgttgtgcgcctgtaatccca//

(SEQ ID NO:65)
ttttttttaaaaaaaaaaaaaaaaagacgtgatctcaggaggatatcccctgtccccattccatttatcagt cctcaattcttattcccctcaaaagtccaagttaccccaaactcctccatttctcctcgacag Intron 9: (SEQ ID NO:66)
Gtaggtgtgcccatccctcatctcacgtacaaagacctaccagaaaagcaattggctccaaagatgtgtccc agcctcccttcccacttcactcccattgtcagatatctctttcatgccaatccaaatttcttacctatttgta ccccccgccccccaagcttgagcatcttcccatactttgtggctgtacagtgtgttgcatatcagccattact ttaccaattctgtgttccttccctgggtttgtatgaatgtttctactagttgggtacctgttagggactttgg gagaccttgtgtatagagaagagttttgtaactgcataactgcctatttgatttgtatagag//

-continued (SEQ ID NO:67)
ccaggagtagagggagagacagaaacagccaacaatggcccagaaaatggatgatatattagataagggaaga aatgagttaccagattggggagagatggtttggatgtcaaagcaggtgatcggtgacgtcagcgtccgaggga agacggctgccaccggcggggccagttgagggaactaggtagttaagtgttgtcgggctaaaagtccctagag tgtccatccctcccccatgtccatgtgcggtaatcccagctcatttaggggccaggcaccaactttggttgcc tttgtgccctcccaggccagcttcctcaacaaccagcacctctgactggatgcctcaggttagacacataaac acattccattgccctgtccgtgccttgtaacaagttcactccctgccttatccctcacaag Intron 10: (SEQ ID NO:68)
Gtgagtgggtcccacacatactacacactaatgcatgaattccatatgcacactacatactaagcctactaat ggcagtatacagattctcacatacaccaccccacctagtagtagtaaagcaactgcccttttactgagcactgg ctaactgcatttcatccttataacagctttgtgtagtagctgatatgcatctcatttttgttgtcagcgcag gtacacatatacattgatgatacacagacttgcacacatacagcagcaggaaaaaacacaaaatgtaaggccg ggcacagtggctcacacctgttatcagcactttggggggccaacgctgggtgaccttccatctttg//

(SEQ ID NO:69)
cacaggaagaatatgaaagatgaatgtctgttgctgttacccagagacactttcacagctaaaaagacatac aaactcatactgactcaccgtctcttactcagcctcagagtgagctgcagtgttggcacacaaatacctcaac acactgctctccttctaaaatattgacaagctccgttacttatatacatggaatgacacacggtctt atccgt tgaaactgtgatatgtagacacaattatgctcacatctagcaattttcagtagatacatgtaaacacacctga atgggtaggacactgcacttgccactacattcccatagcacatcgtggatacatattgccacaatccccaggg actgcaagcacacttttggcaaactgagatcaagatgatagatgtaacttgtagtaccccaccccaaaccct cacttccag Intron 11: (SEQ ID NO:70)
gtgagcccagggtggagggcagggaggtggggaaggaggttgagggctgatactgggcagtgggcttcttgag gggcattagagtgagggaagagaaaacagcggctgtaaccttgtctgactgtag Intron 12: (SEQ ID NO:71)
Gtaaggccttccttcttgaatcccaaaa//

(SEQ ID NO:72)
tacaggcatgagccactgtgcctggccaggaccatatcttaattgtctttgtagtttcagtgtttggtacagt gcctctcactgtttcttttttgcctttgagatcttccctctttgttactgtgatcttccctactggtctttgtt cttctgagtctgtccctatcaccacctcaacccgagctggatgtggcctgtcctcctttttgtgtttctctca cag Intron 13: (SEQ ID NO:73)
gtgagtagaaggaaaaagggagtgcacccagggaggtcagggagagagaatgcagtgtgcaagatggggaaac atggaagatattgaggtcaattggataaagaatgggatggtgggaggaggcagcagaacttcagggaagtatc tggagggtgagagttaaaggaggactgcagggagaattggggcccaaggagagctgaggaacaggacagaggg tgccaggtcctaagaaacagtacttatctcctcag Intron 14: (SEQ ID NO:74)
gtgagtgttgggtgtggatgggcctgtgagccctgcgcagtgatggagtaccatccttggcaggtggtcacca cagctggggatcttcatagcaaccagggcaggagactcacttttgataaccacctgtcttccaccctcgtag Intron 15: (SEQ ID NO:75)
Gtgagggcaggagagtgggtgtagccttcagatgtcttttgggggagatattaggcttatgaaagacatactg gtagataagaaaacttgtggggc//

(SEQ ID NO:76)
atcttttaagctcccttgggatggggaggttccagtaagtctccaaacaagagagtagagtatctcctctttta ctctccccag -continued Intron 16: (SEQ ID NO:77)
gtaagaccctcaacctctgtaaggtgagtgatgaggaaaatgagtcagcagctgaggaagagcgttactctac agcagcactgcccaatatgggatctctcctctgtagttttactctgagctttaccagcactgagacaaaggaa agagaagtcagagttaggggctggaggtgggttagaaagatggggaaggagaggaggaccaagagatgcaaa gtccacagctttgaacccctgtacccag Intron 17: (SEQ ID NO:78)
gtgaggaaaagccagaggttatatgcattgtaagatgtttaaaaaaagcagcagccaggggaaggaggggagt gggcaacttggggatgcttccaacaggcccctcctcttcctgctctctgtctcgctcactctgactctatctt ttcctctgaatgtcttgaggtctcagattgtatctgcaacctgtttccagatcccctaggggcctctgcctc tccttcactttccctggaactgacctccagctcccttcctcacccactcccag Intron 18: (SEQ ID NO:79)
gtaagaatagaggcgggtggaggaatacacatgaggggcccaaaggctacatcttctgggggttcatctatct tgatccacaagccatgcgaggtgcctctccgcccactgcag Intron 19: (SEQ ID NO:80)
gtgaggagaagccctgcagcctgggcctctggcgtctcctgcatctactccaccccttacttgccagccaactc aggctcctgcagctcttctcccatttttctgaccccgctcttcatgaaaggaccatcacccacatccctgtgct tccacctcacatgttcttattctccactggagagccatgctctaatggaactttccgtggcccaaattccttc acctgcctctgagtaggtacacaccactcccaagtatgtctctgcccacgtcccgtgcctcttcactgattct aaattagcccacagggctatggtcaggattcggggaggagagacagagtcagtgtgtctgttacctatttctc ctgtttcaccctgtccatttctctttgatgtgccattcatgccttgagcctcactttcacctcagcccacggc accaggccccaggccctgtctccttccctattcag Intron 20: (SEQ ID NO:81)
gtcaaagggaacaaagggaggtgggattgaggaagggggataatgggaaaggaaccccctgaaaatgctcataac aggaaagcatgccctctgctgcatgccctttatactaaaagtggggagcactaaggtcagagataagaagaat caataccataaacatttcttgaacccttgtttcatgtgagtcactgttggcaaagaggatgaacaaagcgtgc acctcaccattcaagaacttgcagtgcagtagggagggcatgtatacagctttattcacaggccaactgtggt cagtgcgttacgggcttccaatactaacttcccccttgtccaccttatacccagcag Intron 21: (SEQ ID NO:82)
gtgagggagaaactgatgaggggagaaactaaggagggaaaatggaggaggatgaaggagcatgacagtga ggctgggcctctggaatggaatagggctgtgtgggcagaaaagaaatagaacacgagacagggaaaggcagtg caagtgcagaggggcatatggggtccccatggctccgaatgctaacctctgccctctttgcag Intron 22: (SEQ ID NO:83)
gtgaggagaccaatctagctcctcggggaccccaggctgggcatttcccagaggtggggattggctcctcta tcagaacaagggctccctcagcacagagaccacatcccttcccttttctccctccccacaggattggccaagg gtttcaggacaggaaggaggtgattgatgatacactgtcttttattctcttttaag Intron 23: (SEQ ID NO:84)
gtgatgagatccaaatgtgcaaccacctccacatcagagctcccctttcattcctagtcctactgggcctggt ctaggtccacaggatttctgaccccttatttccccttctcttcccactccccttactcctcccaccttcttgc ttgtcctag Intron 24: (SEQ ID NO:85)
gtgcgtatatggccccagtgtctttaccctctctgcatcttctcctgcaactcttctcccccctccagcactt tgcccttcagaaacccaccatttctttctgaaatccctaaatcttcaagatcccaggttttctgtgccacagc ctctcccctctgcccagggatttggttgtccattctgccataaatcttgcgattttctctcttcttcag Sequences of the mMSH5 Intron-exon Junctions The coding sequence (end of exon adjacent to each border) is in capitals and the intronic sequence is lowercase. Consensus splice donor and acceptor sequences are in bold. Phase indicates border phase, which means that the border falls after the indicated base of a codon. For example, given a methionine (ATG) codon: phase of 1 means the border falls between A and T, phase of 2 means the border falls between T and G, while phase of 3 means the border follows the codon.

| INTRON # | phase | length (bp) | | 5' border: | SEQ ID No: |
|---|---|---|---|---|---|
| 10 |  | 279 | GCTGCTCAG | gtatacagtaccacgctccc | 86 |
| 17 |  | 1135 | AGATCCGGG | gtgaggagcccgtggtagga | 87 |
| 18 |  | 279 | GAATGGCAG | gtgagaagggccccatgtc | 88 |
| 19 |  | 3389 | CTCAAGCAG | gtgagggccgccaagctgg | 89 |
| 21 |  | 3180 | ACCAACTCG | gtgcggaggaaaatgaagag | 90 |
| INTRON # | phase | length (bp) | 3' border: | | SEQ ID NO: |
| 10 |  | 279 | ttcccatcccaaccctccag | GCTGTGGTT | 91 |
| 17 |  | 1135 | ctctctctctccttctccag | ACCAGGAGA | 92 |
| 18 |  | 279 | tgtctctctacccaccacag | GCATCCTCT | 93 |
| 19 |  | 3389 | tctcccctgccctggcccag | GTAGGCTTG | 94 |
| 21 |  | 3180 | tcacctctgcccttgacag | GTGGATGGC | 95 |

Sequences of the mMSH5 Introns
Consensus splice donor and acceptor sequences are in bold.

```
Intron 10:                                                         (SEQ ID NO:96)
gtatacagtaccacgctccccaagcaaagtcaagatgagagaagacgtgacttgtaaccttcccatcccaacc ctccag Intron 17:                                                         (SEQ ID NO:97)
gtgaggagcccgtggtaggaggggggcaggctgctctaacagaccctgctctcatgctggcccctctgcatggt cacactgcatctgcatgcctgcttccagatctttccaggcacctctctctctccttctccag Intron 18:                                                         (SEQ ID NO:98)
gtgagaaggggccccatgtcctgctgtggggatcctccctgggtccacaaaccatgcagtgtctctctaccca ccacag Intron 19:                                                         (SEQ ID NO:99)
gtgagggccgccaagctgggggcccacatctccatctcctctggccgccaggccagatcctctgcccccccc cacacacacatacagcacatgtccttgtcctctgagggacagtctgttctttaggatagacctttccgtggcc acaagtccctggaccaacctccaaatagatccatgccgttccctagtatgcctttacccacaaccttgactct ggagttaattgtgaagtcaggacccaggaaactgtgttccagggctctgttcttctgttacactgtgtcctct ctttaatctgtcgttcatgtctttagttgagacccatttttactttgcccatagtacggcaacaggcccatgt tctgtctccctgccctggcccag Intron 21:                                                         (SEQ ID NO:100)
gtgcggaggaaaatgaagagatgctaaggaggggggatggaggaaaatgagaaccgggagcaggagactgacc tcagggaagaaaaggggggatgcgtgcacagaggggaggagaagccatgacagctacagaaggacacagctgtc ctggttctgccctctcacctctgcccttgacag
```

All references mentioned herein are hereby incorporated by reference.

It is evident that those skilled in the art given the benefit of the foregoing disclosure may make numerous other uses and modifications thereof and departures from the specific embodiments described herein without departing from the inventive concepts, and the present invention is to be limited solely by the scope and spirit of the appended claims.

---

What is claimed is:

1. A method of determining an alteration in a nucleic acid encoding human MSH5 gene, wherein said human MSH5 is encoded by SEQ ID No.: 1, the method comprising analyzing a nucleic acid in a biological sample for an alteration in the SEQ ID No.: 1 by comparing the nucleic acid in the biological sample to that of the sequence of SEQ ID NO: 1 wherein a difference in the nucleic acid in the sample compared to SEQ ID NO: 1 represents an alteration in human MSH5 gene.

2. The method of claim 1, wherein the biological sample is selected from blood, tissue, serum, stool, urine, sputum, cerebrospinal fluid, supernatant from cell lysate and a eukaryotic cell sample.

3. The method of claim 1, wherein the analyzing is performed using mRNA in the biological sample.

4. The method of claim 1, wherein the analyzing is performed using DNA in the biological sample.

5. The method of claim 1, wherein the biological sample is from an individual affected with cancer.

6. The method of claim 1, wherein the biological sample is from an individual affected with infertility.

7. The method of claim 1, wherein the alteration is detected using a pair of oligonucleotide primers that hybridize to SEQ ID NOs: 3-26 or 27-50.

8. The method of claim 1, wherein the analysis is performed using nucleic acid sequencing.

9. The method of claim 1, wherein the comparison is made by looking at a genomic sample by looking at at least one individual exon.

10. The method of claim 1, wherein the alteration is determined using restriction fragment length polymorphism using a probe or probes that specifically bind to SEQ ID NO: 1.

11. The method of claim 1, wherein the alteration is a deletion within SEQ ID NO: 1.

12. The method of claim 1, wherein the alteration is a point mutation within SEQ ID NO: 1.

13. A method of determining an alteration in a nucleic acid encoding human MSH5 comprising the steps of
 (a) amplifying a nucleic acid from a biological sample with primers that specifically hybridize to SEQ ID NO:1; and
 (b) comparing the amplified nucleic acid to SEQ ID NO: 1,
 wherein a difference in the nucleic acid from the biological sample compared to the corresponding sequence region in SEQ ID NO: 1 is indicative of an alteration in the nucleic acid encoding human MSH5.

14. The method of claim 13, wherein at least one pair of the primers specifically hybridize to one of the exon/intron borders of human MSH5.

15. The method of claim 14, wherein the human MSH5 exon/intron borders are selected from SEQ ID NOs: 3-26 and 27-50.

16. The method of claim 1, wherein the comparison is made by looking at a coding region of the SEQ ID NO: 1.

17. The method of claim 1, wherein the comparison is made by looking at a non-coding region of the SEQ ID NO: 1.

* * * * *